(12) United States Patent
Morris et al.

(10) Patent No.: US 9,254,141 B2
(45) Date of Patent: Feb. 9, 2016

(54) APPARATUS AND METHOD FOR HEART VALVE REPAIR

(71) Applicant: St. Jude Medical, Inc., St. Paul, MN (US)

(72) Inventors: Benjamin E. Morris, Jeffersonville, IN (US); John Miser, Crestwood, KY (US); Gregory R. Furnish, Louisville, KY (US); Wayne Allen Johnson, Jeffersonville, IN (US); Mark Griffin, Louisville, KY (US)

(73) Assignee: St. Jude Medical, Inc., St. Paul, MN (US)

( * ) Notice: Subject to any disclaimer, the term of this patent is extended or adjusted under 35 U.S.C. 154(b) by 270 days.

(21) Appl. No.: 13/785,695

(22) Filed: Mar. 5, 2013

(65) Prior Publication Data

US 2014/0039511 A1 Feb. 6, 2014

Related U.S. Application Data

(60) Provisional application No. 61/678,897, filed on Aug. 2, 2012.

(51) Int. Cl.
*A61B 17/04* (2006.01)
*A61B 17/22* (2006.01)
(Continued)

(52) U.S. Cl.
CPC ..... *A61B 17/22031* (2013.01); *A61B 17/00234* (2013.01); *A61B 17/0467* (2013.01);
(Continued)

(58) Field of Classification Search
CPC ............. A61B 17/122; A61B 17/1227; A61B 17/128; A61B 17/10; A61B 17/0682; A61B 5/6838; A61B 2017/00584; A61B 2017/0409; A61B 17/0487; A61B 17/08; A61B 17/0057; A61B 17/22031; A61B 17/083; A61B 17/00234; A61B 17/0644; A61B 17/0218; A61B 17/12013; A61B 2017/00243; A61B 2017/00349; A61B 2017/00353; A61B 2017/0078; A61B 2017/00867; A61B 2017/0645; A61B 2017/0649; A61F 2/2454; A61F 2/2466
USPC ................. 606/142–145, 151–152, 155, 157; 128/898; 600/37; 623/2.11, 2.17
See application file for complete search history.

(56) References Cited

U.S. PATENT DOCUMENTS 5,156,608 A  10/1992 Troidl et al.
5,601,573 A  2/1997 Fogelberg et al.
(Continued)

FOREIGN PATENT DOCUMENTS

AU  2002300522 B2  1/2007
WO     9620749 A1  7/1996
(Continued)

OTHER PUBLICATIONS

Merriam-Webster definition of "fabric" as accessed on Dec. 17, 2014; http://www.merriam-webster.com/dictionary/fabric.
(Continued)

*Primary Examiner* — Katrina Stransky
(74) *Attorney, Agent, or Firm* — Lerner, David, Littenberg, Krumholz & Mentlik, LLP

(57) ABSTRACT

A device for transcatheter gathering of tissue of a heart valve leaflet may include an elongated tube extending in a longitudinal direction and a capture tool moveable in the elongated tube between a retracted position and an extended position. The elongated tube may have at least one slot extending generally in the longitudinal direction from a distal end of the elongated tube. The at least one slot may have an open end at the distal end of the elongated tube and a closed end remote therefrom. The capture tool may be operable to gather tissue of the heart valve leaflet into the at least one slot. The gathered tissue may have a pleated configuration.

17 Claims, 16 Drawing Sheets

(51) Int. Cl.
*A61B 17/08* (2006.01)
*A61B 17/00* (2006.01)
*A61B 17/064* (2006.01)
A61B 17/02 (2006.01)
A61B 17/12 (2006.01)
A61F 2/24 (2006.01)

(52) U.S. Cl.
CPC ........... *A61B17/0644* (2013.01); *A61B 17/083* (2013.01); *A61B 17/0218* (2013.01); *A61B 17/12013* (2013.01); *A61B 2017/00243* (2013.01); *A61B 2017/00349* (2013.01); *A61B 2017/00353* (2013.01); *A61B 2017/00783* (2013.01); *A61B 2017/00867* (2013.01); *A61B 2017/0645* (2013.01); *A61B 2017/0649* (2013.01); *A61F 2/2454* (2013.01); *A61F 2/2466* (2013.01)

(56) References Cited

U.S. PATENT DOCUMENTS

| | | |
|---|---|---|
| 5,749,879 A | 5/1998 | Middleman et al. |
| 5,921,993 A | 7/1999 | Yoon |
| 6,440,152 B1 | 8/2002 | Gainor et al. |
| 6,569,182 B1 | 5/2003 | Balceta et al. |
| 6,752,813 B2 | 6/2004 | Goldfarb et al. |
| 6,945,978 B1 | 9/2005 | Hyde |
| 7,011,669 B2 | 3/2006 | Kimblad |
| 7,464,712 B2 | 12/2008 | Oz et al. |
| 7,569,062 B1 | 8/2009 | Kuehn et al. |
| 7,758,595 B2 | 7/2010 | Allen et al. |
| 8,777,966 B2 | 7/2014 | Dale et al. |
| 2001/0016750 A1 | 8/2001 | Malecki et al. |
| 2002/0013571 A1 | 1/2002 | Goldfarb et al. |
| 2002/0107531 A1 | 8/2002 | Schreck et al. |
| 2003/0093071 A1 | 5/2003 | Hauck et al. |
| 2004/0039442 A1 | 2/2004 | St. Goar et al. |
| 2004/0181238 A1 | 9/2004 | Zarbatany et al. |
| 2004/0193185 A1 | 9/2004 | McBrayer |
| 2005/0090837 A1 | 4/2005 | Sixto et al. |
| 2005/0096671 A1 | 5/2005 | Wellman et al. |
| 2005/0107871 A1* | 5/2005 | Realyvasquez et al. ...... 623/2.11 |
| 2005/0125011 A1 | 6/2005 | Spence et al. |
| 2005/0143763 A1 | 6/2005 | Ortiz et al. |
| 2005/0149072 A1 | 7/2005 | DeVries et al. |
| 2005/0177176 A1 | 8/2005 | Gerbi et al. |
| 2005/0251161 A1 | 11/2005 | Saadat et al. |
| 2006/0122633 A1 | 6/2006 | To et al. |
| 2006/0173422 A1 | 8/2006 | Reydel et al. |
| 2007/0049952 A1 | 3/2007 | Weiss |
| 2007/0102474 A1 | 5/2007 | Shelton et al. |
| 2007/0102475 A1 | 5/2007 | Ortiz et al. |
| 2007/0142846 A1 | 6/2007 | Catanese et al. |
| 2007/0162056 A1 | 7/2007 | Gerbi et al. |
| 2007/0197858 A1 | 8/2007 | Goldfarb et al. |
| 2007/0225734 A1 | 9/2007 | Bell et al. |
| 2008/0125796 A1* | 5/2008 | Graham ........................ 606/142 |
| 2008/0294175 A1 | 11/2008 | Bardsley et al. |
| 2008/0300624 A1 | 12/2008 | Schwemberger et al. |
| 2009/0062852 A1 | 3/2009 | Marino |
| 2009/0118744 A1 | 5/2009 | Wells et al. |
| 2009/0125038 A1 | 5/2009 | Ewers et al. |
| 2009/0149870 A1 | 6/2009 | Jugenheimer et al. |
| 2011/0054521 A1* | 3/2011 | Ventura et al. ................. 606/216 |
| 2011/0077668 A1* | 3/2011 | Gordon et al. ................. 606/142 |
| 2011/0087242 A1 | 4/2011 | Pribanic et al. |
| 2011/0114700 A1 | 5/2011 | Baxter, III et al. |
| 2011/0230897 A1 | 9/2011 | Palermo et al. |
| 2011/0313432 A1 | 12/2011 | Miles et al. |
| 2012/0226291 A1 | 9/2012 | Malizia et al. |
| 2013/0046332 A1 | 2/2013 | Jones et al. |
| 2014/0039607 A1 | 2/2014 | Kovach |

FOREIGN PATENT DOCUMENTS

| | | |
|---|---|---|
| WO | 9900059 A1 | 1/1999 |
| WO | 0128432 A1 | 4/2001 |
| WO | 0139672 A2 | 6/2001 |
| WO | 0182847 A2 | 11/2001 |
| WO | 0200121 A1 | 1/2002 |
| WO | 03049619 A2 | 6/2003 |
| WO | 2006039199 A2 | 4/2006 |
| WO | 2007027451 A2 | 3/2007 |
| WO | 2008068756 A2 | 6/2008 |
| WO | 2008121738 A2 | 10/2008 |
| WO | 2009087592 A2 | 7/2009 |
| WO | 2010094896 A1 | 8/2010 |
| WO | 2011053673 A1 | 5/2011 |
| WO | 2012087724 A1 | 6/2012 |
| WO | 2012106398 A1 | 8/2012 |
| WO | 2013019415 A1 | 2/2013 |
| WO | 2013116617 A1 | 8/2013 |
| WO | 2014022464 A1 | 2/2014 |

OTHER PUBLICATIONS

International Search Report and Written Opinion for Application No. PCT/US2013/052843 dated Oct. 11, 2013.
International Search Report and Written Opinion for Application No. PCT/US2013/052838 dated Oct. 11, 2013.
International Search Report and Written Opinion for Application No. PCT/US2013/052822 dated Jan. 21, 2014.
International Preliminary Report on Patentability for Application No. PCT/US2012/023437 dated Aug. 6, 2013.
International Search Report for Application No. PCT/US2013/023077 dated May 14, 2013.
International Search Report and Written Opinion for Application No. PCT/US2013/023082 dated Oct. 1, 2013.
International Search Report and Written Opinion for Application No. PCT/US2013/024304 dated Jul. 5, 2013.
International Search Report for Application No. PCT/US2013/052832 dated Jan. 15, 2014.
International Search Report for Application No. PCT/US2012/023437 dated Apr. 24, 2012.
International Search Report and Written Opinion for Application No. PCT/US2013/065360 dated Apr. 23, 2014.

* cited by examiner

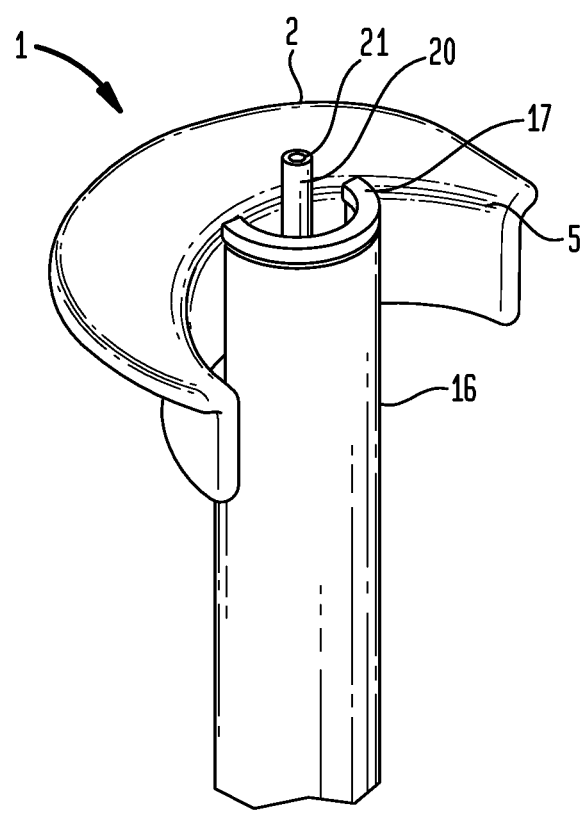

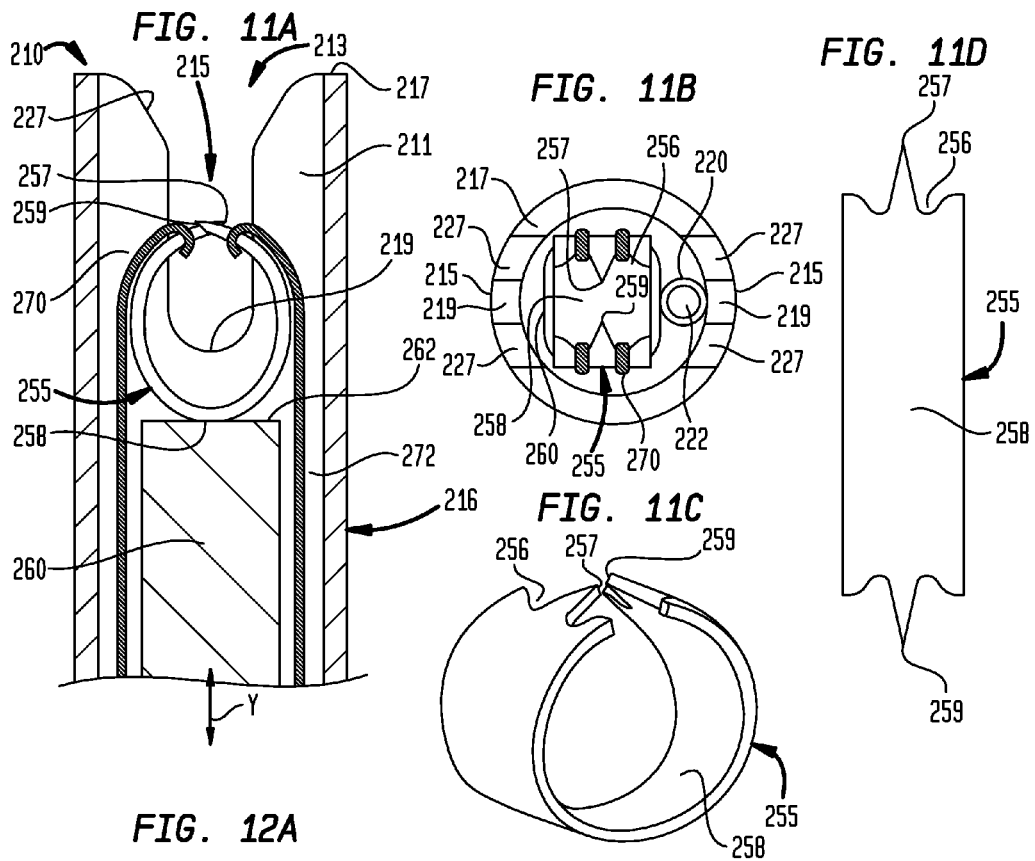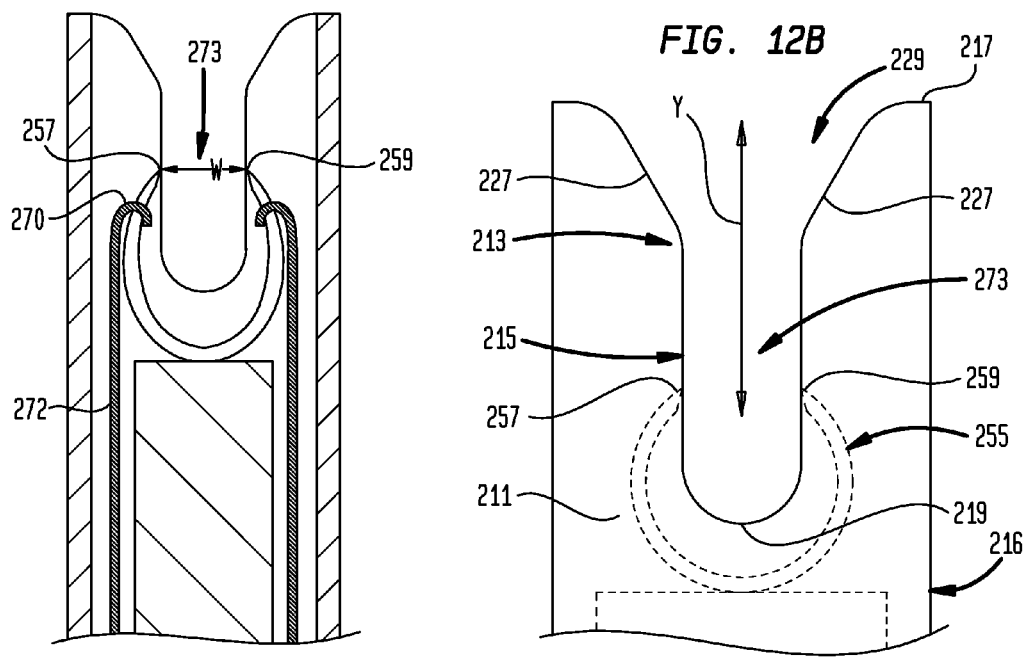

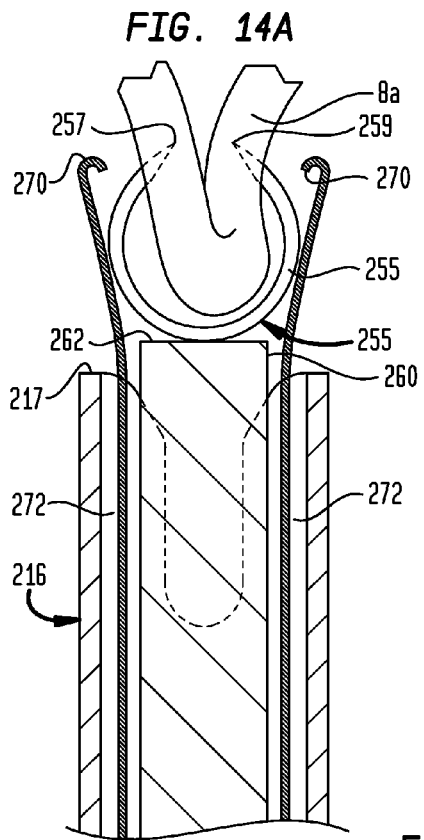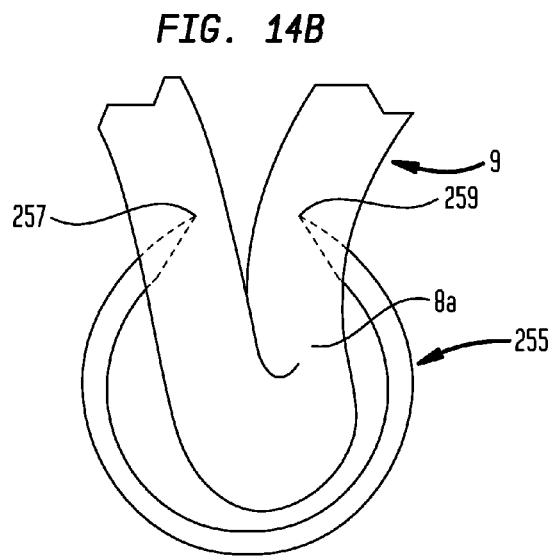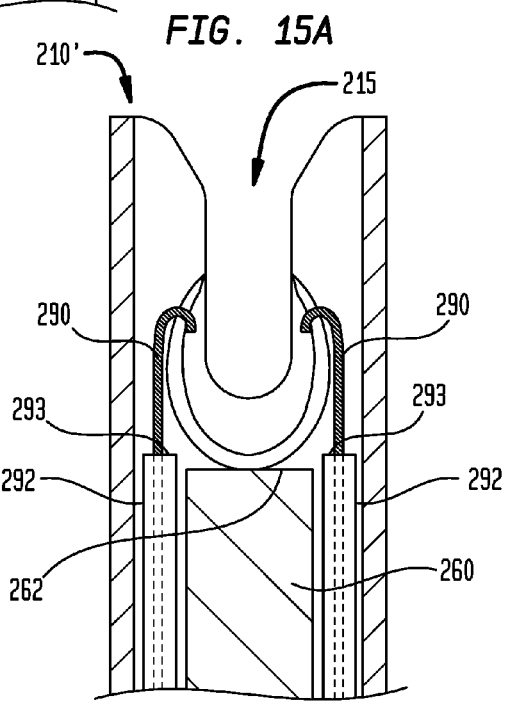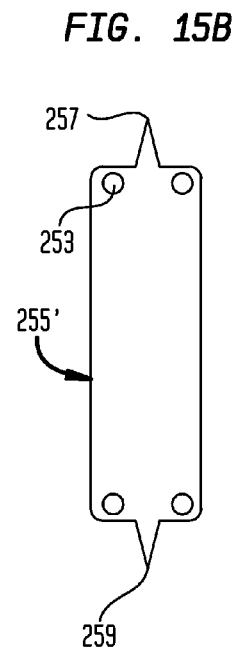

APPARATUS AND METHOD FOR HEART VALVE REPAIR

CROSS-REFERENCE TO RELATED APPLICATION

The present application claims the benefit of the filing date of U.S. Provisional Patent Application No. 61/678,897 filed Aug. 2, 2012, the disclosure of which is hereby incorporated herein by reference.

BACKGROUND OF THE INVENTION

The present invention is related to heart valve repair, and more particularly to devices, systems, and methods for transcatheter repair of a heart valve leaflet.

Properly functioning heart valves can maintain unidirectional blood flow in the circulatory system by opening and closing, depending on the difference in pressure on each side of the valve. The two atrioventricular valves (mitral and tricuspid valves) are multicusped valves that prevent backflow from the ventricles into the atria during systole. They are anchored to the wall of the ventricle by chordae tendinae, which prevent the valve from inverting.

The mitral valve is located at the gate of the left ventricle and is made up of two leaflets and a diaphanous incomplete ring around the valve, known as the mitral valve annulus. When the valve opens, blood flows into the left ventricle. After the left ventricle fills with blood and contracts, the two leaflets of the mitral valve are pushed upwards and close, preventing blood from flowing back into the left atrium and the lungs.

Mitral valve prolapse is a type of myxomatous valve disease in which the abnormal mitral valve leaflets prolapse (i.e., a portion of the affected leaflet may be billowed, loose, and floppy). Furthermore, the chordae tendinae may stretch and thus become too long, or the chordae tendinae may be broken. As a result, the valve does not close normally. As a result of being stretched, the unsupported valve leaflet bulges back, or "prolapses," into the left atrium like a parachute. Thus, as the ventricle contracts, the abnormal leaflet may be propelled backwards, beyond its normal closure line into the left atrium, thereby allowing blood to return back into the left atrium and the lungs.

Mitral valve prolapse causes mitral regurgitation. Isolated posterior leaflet prolapse of the human heart mitral valve, i.e. prolapse of a single leaflet, is the most common cause of mitral regurgitation. The exact cause of the prolapse is not clear. Untreated mitral regurgitation may lead to congestive heart failure and pulmonary hypertension.

Despite the various improvements that have been made to devices and methods for mitral valve leaflet repair, there remain some shortcomings. For example, conventional methods of treating mitral valve prolapse include replacement of the mitral valve, clipping the two mitral valve leaflets to one another, and resection of the prolapsed segment using open heart surgery. Such surgical methods may be invasive to the patient and may require an extended recovery period.

There therefore is a need for further improvements to the current techniques for treating heart valve leaflet prolapse. Among other advantages, the present invention may address one or more of these needs.

Patents relevant to devices, systems, and methods for transcatheter repair of heart valve leaflets include U.S. Pat. Nos. 6,752,813, 7,464,712, and 7,758,595.

BRIEF SUMMARY OF THE INVENTION

Devices and methods for transcatheter gathering of tissue of a heart valve leaflet are disclosed. A device for transcatheter gathering of tissue of a heart valve leaflet may include an elongated tube extending in a longitudinal direction and a capture tool moveable in the elongated tube between a retracted position and an extended position. The elongated tube may have at least one slot extending generally in the longitudinal direction from a distal end of the elongated tube. The at least one slot may have an open end at the distal end of the elongated tube and a closed end remote therefrom. The capture tool may be operable to gather tissue of the heart valve leaflet into the at least one slot. The gathered tissue may have a pleated configuration.

A distal end of the capture tool may have a hook shape. The capture tool may include a grasping wire slidably disposed in a containment tube. A distal portion of the grasping wire may be adapted to change from a linear shape to the hook shape when the distal portion of the grasping wire is extended out from the containment tube. The grasping wire may be partially or entirely made from a shape-memory material. The device may also include an operating handle having an actuating member adapted to control movement of the capture tool between the retracted and extended positions.

At least a portion of the at least one slot may have a generally U-shaped configuration. The elongated tube may have at least one pair of opposed angled portions. Each pair of opposed angled portions may extend between the distal end of the elongated tube and sidewalls of a corresponding one of the at least one slot. Each pair of angled portions may form at least a portion of a substantially V-shaped opening leading to the at least one slot. The at least one slot may include two slots located substantially opposite one another in a direction perpendicular to the longitudinal direction of the elongated tube.

The device may also include a tissue securing component disposed within the elongated tube and adapted to be applied to the gathered tissue for holding the gathered tissue in the pleated configuration. The tissue securing component may comprise a clip arrangeable in a partially-open condition within the elongated tube and biased to contract to a clamping condition when deployed from the elongated tube. The clip may be wholly or partly made of a shape-memory material. The device may also include retention elements adapted to hold the clip in the partially-open condition. The retention elements may include hooks adapted to engage with recesses at opposed ends of the clip. The retention elements may include sutures adapted to engage with apertures at opposed ends of the clip. The device may also include cutting tubes disposed around the sutures. The cutting tubes may be adapted to slide in the longitudinal direction relative to the elongated tube. The cutting tubes may each have a sharp distal end adapted to cut through a portion of a corresponding one of the sutures.

The device may also include a support shelf slidable within the elongated tube in the longitudinal direction between a retracted position in which a distal end of the support shelf is disposed within the elongated tube and an extended position in which the distal end of the support shelf is disposed beyond the distal end of the elongated tube. The support shelf being may be adapted to support the clip within the elongated tube. The clip in the partially-open condition may have a generally cylindrical shape and may defines a longitudinal axis around which the clip extends. The device may also include retention elements adapted to hold the clip in the partially-open condition with the longitudinal axis of the clip oriented substantially perpendicular to the longitudinal direction.

Another device for transcatheter gathering of tissue of a heart valve leaflet may include an elongated tube extending in a longitudinal direction, a clip disposed within the elongated tube and adapted to be applied to gathered tissue for holding the gathered tissue in a gathered configuration, a support shelf slidable within the elongated tube in the longitudinal direction, and a plurality of retention elements adapted to hold the clip in a partially-open condition with a longitudinal axis of the clip oriented substantially perpendicular to the longitudinal direction.

The clip may be arrangeable in the partially-open condition within the elongated tube and may be biased to contract to a clamping condition when deployed from the elongated tube. The clip in the partially-open condition may have a generally cylindrical shape and may define the longitudinal axis around which the clip extends. The support shelf may be slidable between a retracted position in which a distal end of the support shelf is disposed within the elongated tube and an extended position in which the distal end of the support shelf is disposed beyond a distal end of the elongated tube. The support shelf may be adapted to support the clip within the elongated tube.

The device may also include a capture tool moveable in the elongated tube between a retracted position and an extended position. The capture tool may be operable to draw the tissue of the heart valve leaflet into the elongated tube. The elongated tube may have at least one slot extending generally in the longitudinal direction from a distal end of the elongated tube. The at least one slot may have an open end at the distal end of the elongated tube and a closed end remote therefrom. The at least one slot may be adapted to form the gathered tissue into a pleated configuration.

A tissue securing component for gathering tissue of a heart valve leaflet may include a clip wholly or partly made of a shape-memory material. The clip may include a flat sheet having a central portion and two end portions at opposite ends of the central portion. The end portions may each have a prong extending from an edge thereof. Each end portion may have at least one recess extending from the edge thereof inward toward the central portion. Each recess may have an open end at the edge of its end portion and a closed end remote therefrom. The clip may be biased to move from a partially-open condition with the prongs spaced apart from one another by a gap to a substantially round clamping condition where the prongs are adjacent one another such that the gap is reduced or eliminated. The clip may be adapted to be applied to heart valve leaflet tissue to hold the tissue in a gathered configuration.

A transcatheter method of gathering tissue of a heart valve leaflet may include inserting a catheter assembly to a position adjacent the heart valve leaflet. The catheter assembly may include an elongated tube extending in a longitudinal direction and a capture tool moveable between a retracted position and an extended position. The elongated tube may have at least one slot having an open end at a distal end of the elongated tube and a closed end remote therefrom. The method may also include moving the capture tool from the retracted position to the extended position and manipulating the capture tool so that tissue of the heart valve leaflet is captured by the capture tool. The method may also include retracting the capture tool from the extended position toward the retracted position to draw the captured tissue into the at least one slot in a pleated configuration and securing the captured tissue with a tissue securing component to hold the captured tissue substantially in the pleated configuration.

The capture tool may include a grasping wire slideably disposed in a containment tube. The method may also include sliding a distal portion of the grasping wire out from the containment tube so that the distal portion of the grasping wire changes from a linear shape to a hook shape. At least a portion of the at least one slot may have a generally U-shaped configuration. The pleated condition may at least partially conform to the shape of the at least one slot. The at least one slot may include two slots located substantially opposite one another in a direction perpendicular to the longitudinal direction of the elongated tube. The retracting step may draw the captured tissue at least partially into both of the slots.

The tissue securing component may include a clip arrangeable in a partially-open condition within the elongated tube and biased to contract to a clamping condition when deployed from the tube. The securing step may release the clip for movement from the partially-open condition to the clamping condition around the captured tissue. The method may also include, before the securing step, holding the clip in the partially-open condition by tensioning retention elements engaged with the clip at opposed ends thereof. The securing step may release the clip to the clamping condition by releasing tension exerted by the retention elements. The clip in the partially-open condition may be disposed adjacent a distal end of a support shelf slidable within the elongated tube in the longitudinal direction. The method may also include sliding the support shelf in the longitudinal direction relative to the elongated tube until the clip is disposed outside of the elongated tube. The method may also include withdrawing the catheter assembly from the patient and leaving the tissue securing component attached to the tissue.

Another transcatheter method of gathering tissue of a heart valve leaflet may include inserting an elongated tube to a position adjacent the heart valve leaflet and capturing tissue of the heart valve leaflet. The elongated tube may include at least one slot having an open end at a distal end of the elongated tube. The method may also include drawing the captured tissue into the at least one slot in a pleated configuration and securing the captured tissue to hold the captured tissue substantially in the pleated configuration. The capturing step may be performed by manipulating a capture tool so that the tissue of the heart valve leaflet is captured by the capture tool. The capture tool may include a grasping wire including a distal portion having a hook shape. The securing step may be performed by clamping a clip around at least a portion of the captured tissue.

BRIEF DESCRIPTION OF THE DRAWINGS

Various embodiments of the present invention will now be discussed with reference to the appended drawings. It is appreciated that these drawings depict only some embodiments of the invention and are therefore not to be considered limiting of its scope.

FIG. 3 is a perspective view of the distal portion of the device of FIG. 2A, shown with the containment tube deployed;

FIG. 11A is a diagrammatic view of the distal portion of another embodiment of a device for transcatheter gathering of heart valve leaflet tissue, shown with the clip in an initial position;

FIG. 11B is a top plan view of the distal portion of the device shown in FIG. 11A;

FIG. 11C is a perspective view of the clip of FIG. 11A, shown in a closed position;

FIG. 11D is a plan view of the clip of FIG. 11A, shown in an open position;

FIGS. 12A and 12B are a longitudinal cross-sectional view and a side view of the distal portion of the device of FIG. 11A, shown with the clip in a partially-open condition;

FIG. 14A is a diagrammatic view of the distal portion of the device of FIG. 11A, shown with the clip released from the device;

FIG. 14B is a diagrammatic view of the clip and the posterior mitral valve leaflet of FIG. 11A, shown with the clip in a deployed position;

FIG. 15A is a diagrammatic view of the distal portion of yet another embodiment of a device for transcatheter gathering of heart valve leaflet tissue, shown with the clip in an partially-open position; and FIG. 15B is a plan view of the clip of FIG. 15A, shown in an open position.

DETAILED DESCRIPTION

As used herein, the terms "proximal" and "distal" are to be taken as relative to a user (e.g., a surgeon or an interventional cardiologist) using the disclosed transcatheter devices. "Proximal" is to be understood as relatively close to the user and "distal" is to be understood as relatively farther away from the user. The invention will be described in connection with the repair of a mitral valve leaflet, but it may be useful in the repair of other types of cardiac valves or in the gathering and clamping of other types of loose body tissue.

Figure 1:
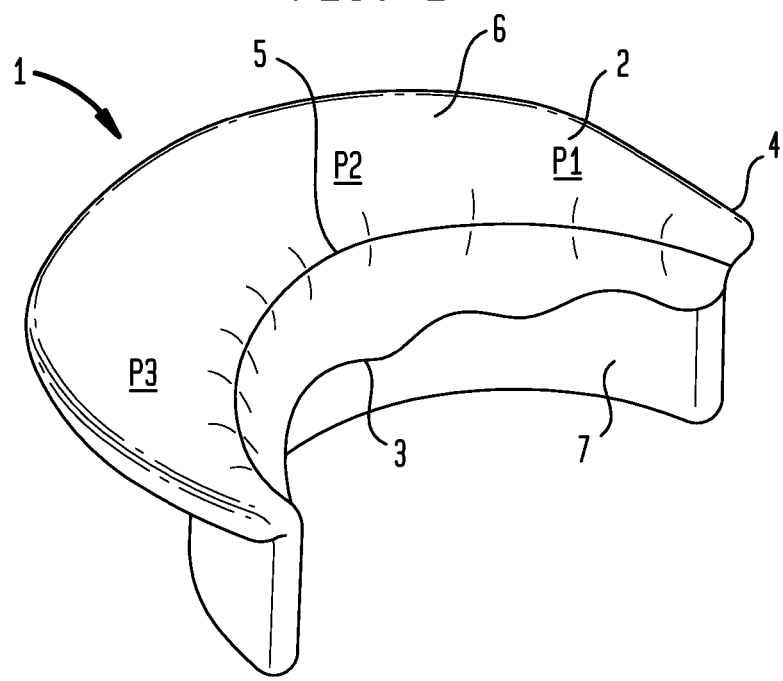
FIG. 1 is a diagrammatic perspective view of the posterior leaflet of a mitral valve.

Referring to FIG. 1, an exemplary mitral valve 1 includes a posterior leaflet 2 and an anterior leaflet 3. The leaflets 2 and 3 extend from an annulus 4 to a coaption line 5 where the leaflets meet. The posterior leaflet 2 has an upper portion 6 that is generally perpendicular to the direction of blood flow through the valve 1 and extends between the annulus and the coaption line 5. Additionally, the posterior leaflet 2 has a lower portion 7 that is generally parallel to the direction of blood flow through the valve 1 and extends below the coaption line 5. The posterior leaflet 2 has three scalloped portions P1, P2, and P3, any of which may include a portion that is billowed, loose, or floppy, and therefore be the cause of a prolapse condition of the valve. The inventive devices, systems, and methods described herein may be adapted to repair such a billowed, loose, or floppy portion of the posterior leaflet 2 or the anterior leaflet 3.

Figure 2A:
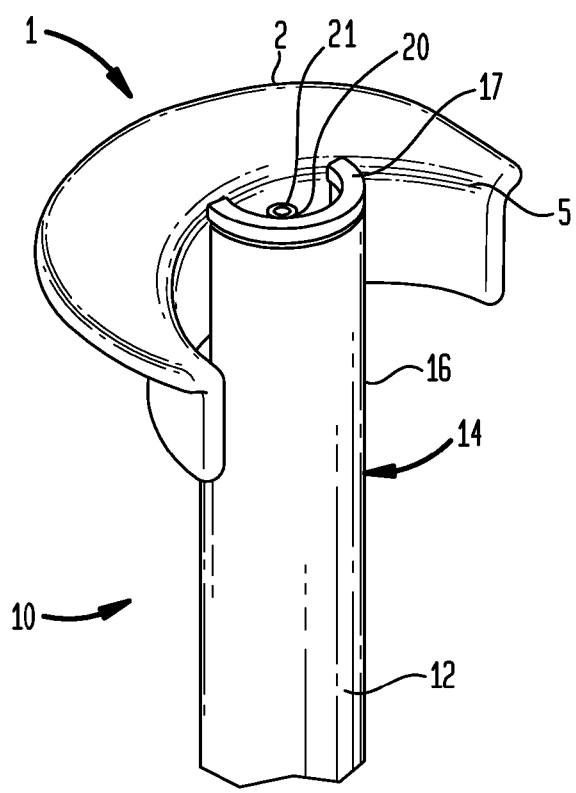
FIG. 2A is a perspective view of the distal portion of one embodiment of a device for transcatheter gathering of heart valve leaflet tissue, engaged with the posterior leaflet of the mitral valve of FIG. 1.

Referring to FIG. 2A, an exemplary device 10 for transcatheter gathering of heart valve leaflet tissue includes an elongated catheter assembly 12 adapted to be inserted through the apex of a human heart so that a distal portion 14 of the catheter assembly may reach the patient's mitral valve 1 for repair thereof.

The catheter assembly 12 includes a containment tube disposed within an outer tube 16 and longitudinally slidable therein between a retracted position within the outer tube and a deployed position in which a distal tip 21 of the containment tube protrudes distally beyond the distal edge 17 of the outer tube (FIG. 3). In a particular embodiment, the outer tube 16 may be made of one or more echogenic materials, so that the outer tube may be more easily visualized inside a patient using three-dimensional echocardiography.

Figure 4A:
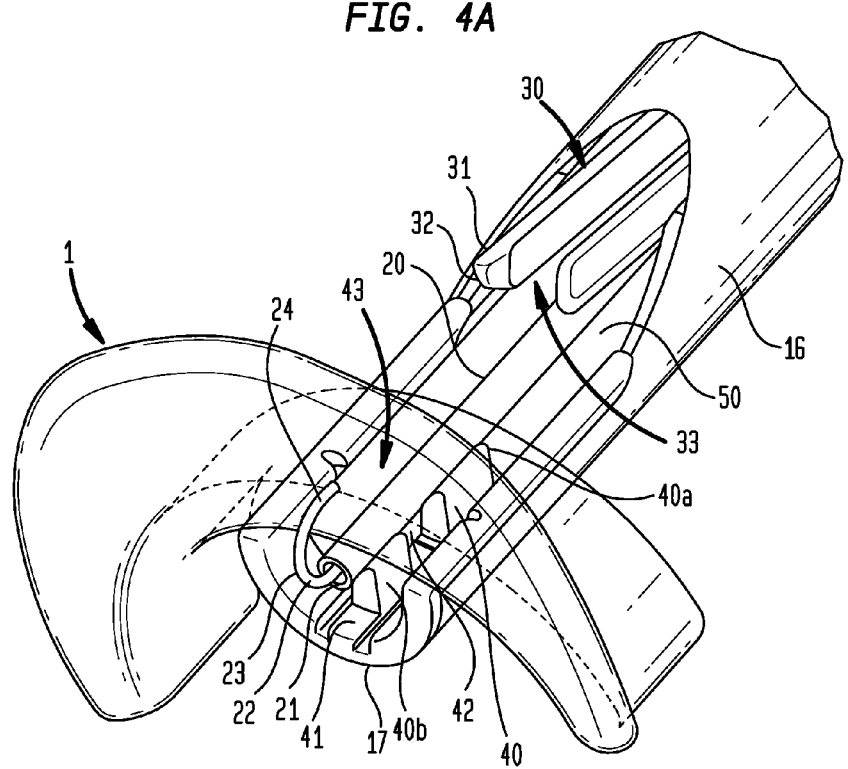
FIGS. 4A and 4B are a perspective view and a longitudinal cross-sectional view of the distal portion of the device of FIG. 2A, shown with the hook deployed.
Figure 4B:
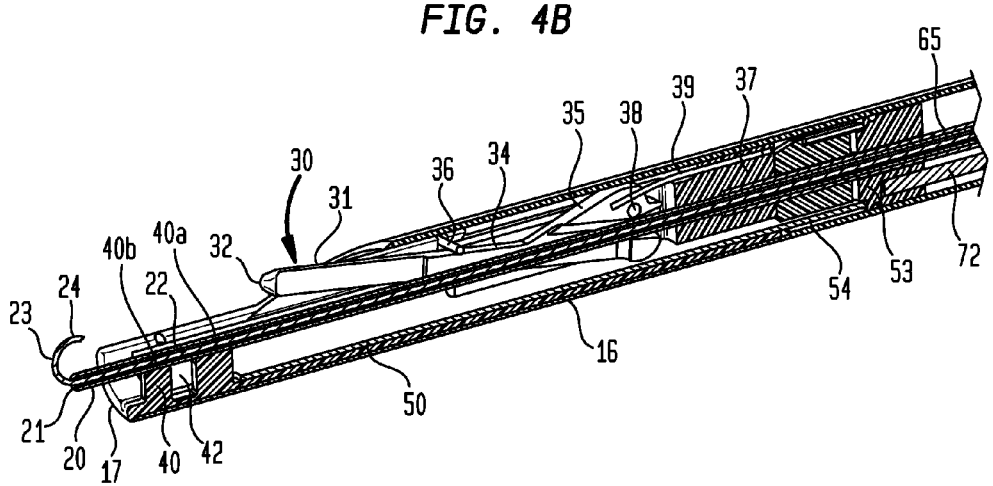

The catheter assembly 12 further includes a capture tool in the form of a grasping wire 22 (FIGS. 4A and 4B) that is longitudinally slidable within the containment tube 20 between a retracted position substantially entirely within the lumen of the containment tube (FIGS. 2 and 3), and a deployed position in which a distal portion 23 of the grasping wire protrudes from the distal tip of the containment tube (FIGS. 4A and 4B). The grasping wire 22 may have a linear configuration when fully retracted within the containment tube 20 and the distal portion 23 thereof may assume the shape of a hook 24 when deployed from the containment tube. In that regard, the grasping wire 22 may be formed from a memory metal or a strong, resilient metal or polymer that will cause the hook 24 to form automatically when deployed.

Figure 8A:
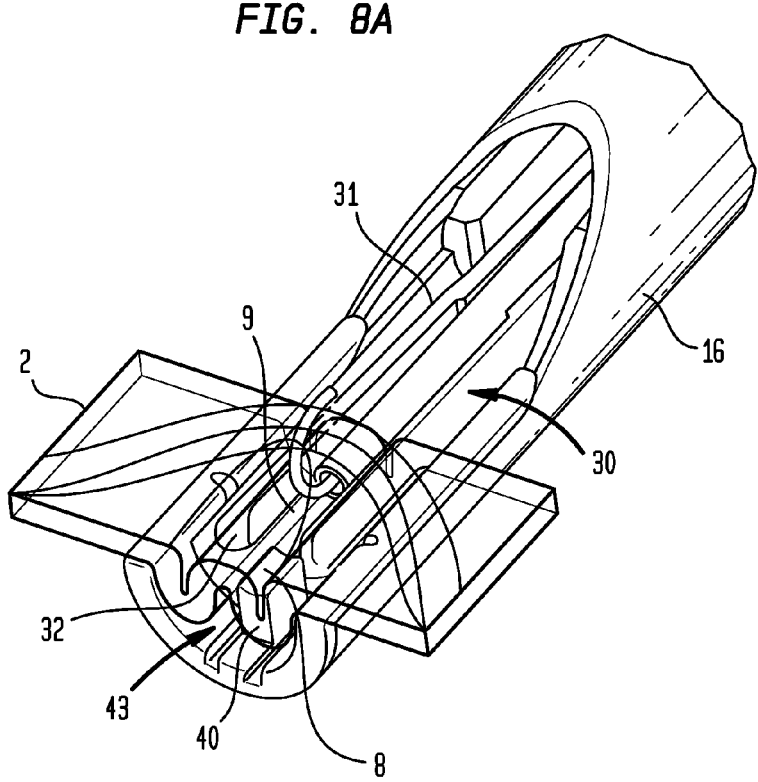
FIGS. 8A and 8B are a perspective view and a longitudinal cross-sectional view of the distal portion of the device of FIG. 2A, shown with the hook in the partially-retracted position and the fork in the tissue-capturing position.

The catheter assembly 12 further includes a clamping member in the form of a fork 30 (FIGS. 4A and 4B) that is longitudinally slidable within the outer tube 16 between an initial or retracted position (FIG. 4A) and a tissue-capturing position (FIG. 8A). The fork 30 includes two tines 31 having respective ends 32, the tines being spaced apart from one another by an internal gap 33. The fork 30 further includes first cam surfaces 34 that are the top surfaces of the tines and a second cam surface 35 located proximally of the tines. The cam surfaces 34 and 35 are adapted to cooperate with a pin 36 attached to the outer tube 16 and orientated substantially orthogonal to the longitudinal direction of travel of the fork 30 to control transverse movement of the fork relative to the outer tube 16, as will be explained below.

At its distal end 17, the outer tube 16 has an open side that provides clearance for the fork 30 to move away from the closed side 41 of the outer tube. A tissue support in the form of an anvil 40 (FIGS. 4A and 4B) is mounted on the closed side 41 of the outer tube 16 so as to lie between the closed side 41 and the containment tube 20 when the containment tube is in the deployed position. The anvil 40 has a proximal portion 40a and a distal portion 40b, with a gap 42 defined therebetween. The widths of the portions 40a and 40b are such that the anvil 40 may be received between the tines 31 of the fork 30 during the use of the device 10 to repair the valve leaflet.

Figure 8B:
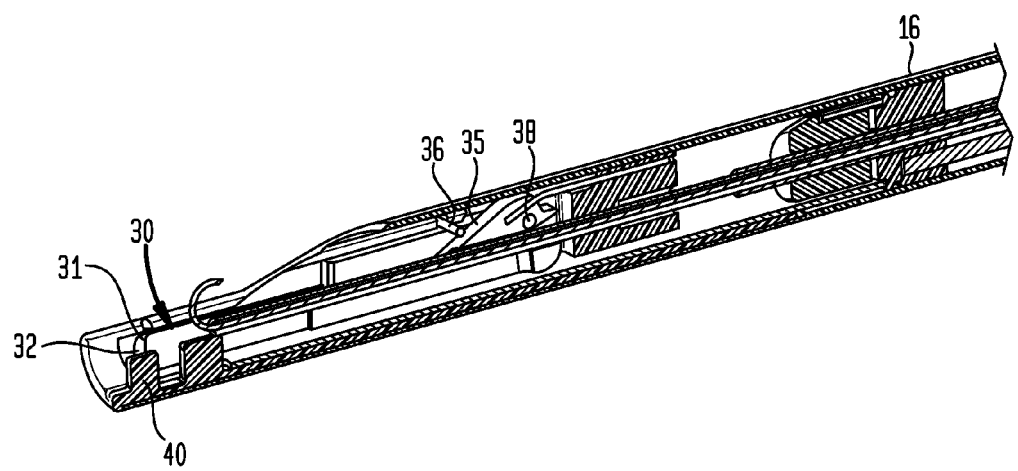
Figure 8C:
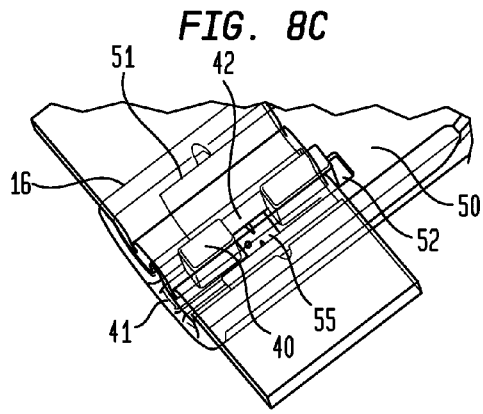
FIG. 8C is a view similar to FIG. 8A, but with portions removed to illustrate the interior of the distal portion.
Figure 9:
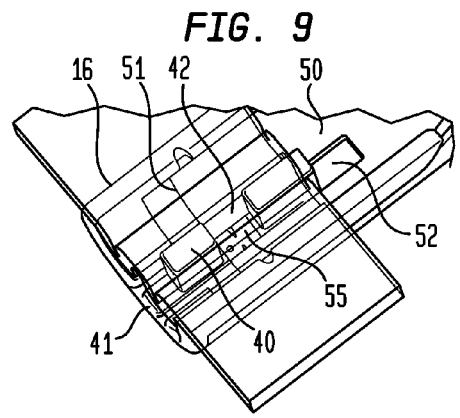
FIG. 9 is a view similar to FIG. 8C, but shown with the retaining arm in a partially-retracted position.
Figure 10A:
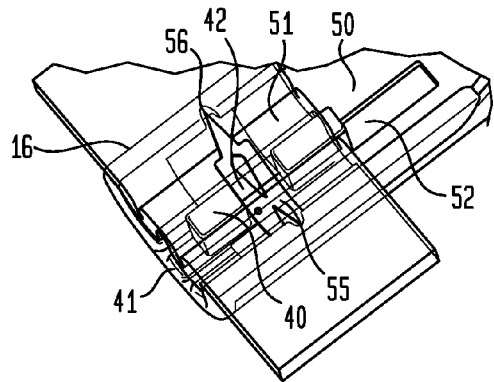
FIG. 10A is a view similar to FIG. 8A, but shown with the retaining arm in the retracted position.

The catheter assembly 12 further includes a retaining arm 50 (FIGS. 4A and 4B) disposed within the outer tube 16 and longitudinally slidable therein between an initial position (FIG. 8C) and a retracted position (FIG. 10A). The retaining arm 50 includes a pair of fingers 51 separated by an elongated slot 52. The slot 52 is sized to receive the anvil 40 when the retaining arm 50 is in the initial position shown in FIG. 8C. In this initial position, the fingers 51 lie on either side of the anvil 40 and engage a clip 55 disposed within the gap 42, holding it in place against the closed side of 41 of the outer tube 16. The retraction of the retaining arm 50 releases the clip 55 for application to tissue.

The clip 55 (FIG. 10A) may be made of a memory metal and may be biased to curl into a substantially round configuration (FIG. 10B) when the retaining arm 50 is retracted proximally and the fingers 51 no longer overlie the clip. A prong 56 at each end of the clip 55 is adapted to become embedded in the leaflet tissue when the clip is deployed.

Figure 2B:
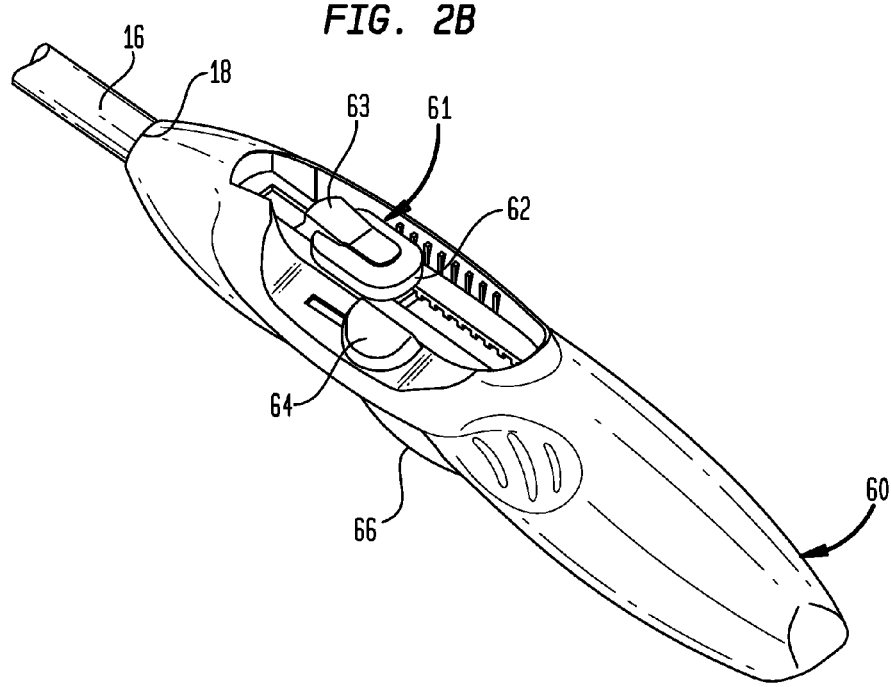
FIGS. 2B and 2C are a perspective view and a longitudinal cross-sectional view of one embodiment of a handle suitable for controlling the device of FIG. 2A, shown with the buttons positioned to correspond to the positions of the components of the device shown in FIG. 2A.
Figure 2C:
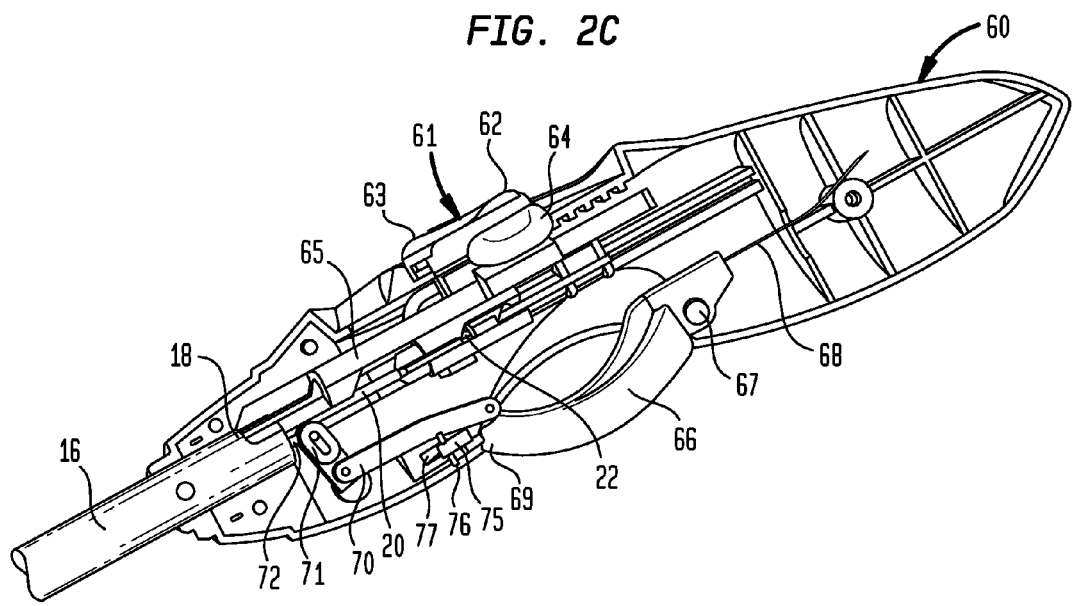

Referring now to FIGS. 2B and 2C, the device 10 further includes a handle 60 at the proximal end 18 of the outer tube 16. The handle 60 includes a first button 61, a second button 64, and a third button 66 for controlling the operation of the containment tube 20, the grasping wire 22, the fork 30, and the retaining arm 50. The first button 61 has a first portion 62 and a second portion 63 that are moveable longitudinally relative to the handle 60 and relative to one another. The first portion 62 is attached to the containment tube 20, such that sliding movement of the first portion in a proximal or distal direction results in a corresponding sliding movement of the containment tube. The second portion 63 is attached to the grasping wire 22, such that sliding movement of the second portion in a proximal or distal direction results in a corresponding sliding movement of the grasping wire. The containment tube 20 and the grasping wire 22 may be moved together by the simultaneous movement of the first and second portions of the button 61. Alternatively, the containment tube 20 and the grasping wire 22 may be moved independently of one another by moving one of the portions of the button 61 while the other portion remains stationary. For example, sliding the second portion 62 distally while the first portion 63 remains stationary advances the grasping wire 22 out from the containment tube 20, resulting in deployment of the hook 24.

The second button 64 is moveable longitudinally relative to the handle 60 for controlling the movement of the fork 30 relative to the outer tube 16. The second button 64 is attached to one end of a linkage 65, the other end of which is attached to a coupling block 37 (FIG. 4B) positioned in the distal portion 14 of the catheter assembly 16. The coupling block 37, in turn, is coupled to the fork 30 via a pivot pin and a spring 39 that extends between the fork and the coupling block. The spring 39 is biased to rotate the fork 30 about the pivot pin 38 so that the tines 31 of the fork move laterally away from the closed side 41 of the outer tube 16.

The third button 66 has a trigger shape and is connected at one end to the handle 60 by a pivot pin 67 that allows for movement of the button in a lateral direction relative to the longitudinal axis of the handle for controlling the movement of the retaining arm 50 relative to the outer tube 16. A spring 68 biases the third button 66 to return to its initial position (FIG. 2C) after the button has been actuated (FIG. 10D). The opposite end 69 of the third button 66 is pivotally coupled to a linkage assembly including a first linkage 70, a second linkage 71, and a third linkage 72, all of which are pivotally connected to one another in series. The third linkage 72 is attached to a coupling block positioned in the distal portion 14 of the catheter assembly 12. The coupling block 53, in turn, is attached to a proximal end 54 (FIG. 4B) of the retaining arm 50, such that actuation of the third button 66 may cause the third linkage to slide proximally to retract the retaining arm and thereby deploy the clip 55 (FIG. 10B).

Figure 8D:
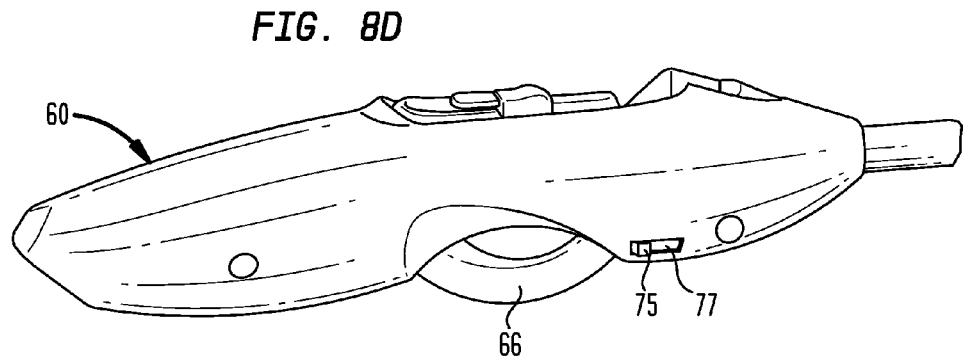
FIGS. 8D and 8E are a perspective view and a longitudinal cross-sectional view of the handle of FIG. 2B, shown with the buttons positioned to correspond to the positions of the components of the device shown in FIG. 8A.
Figure 8E:
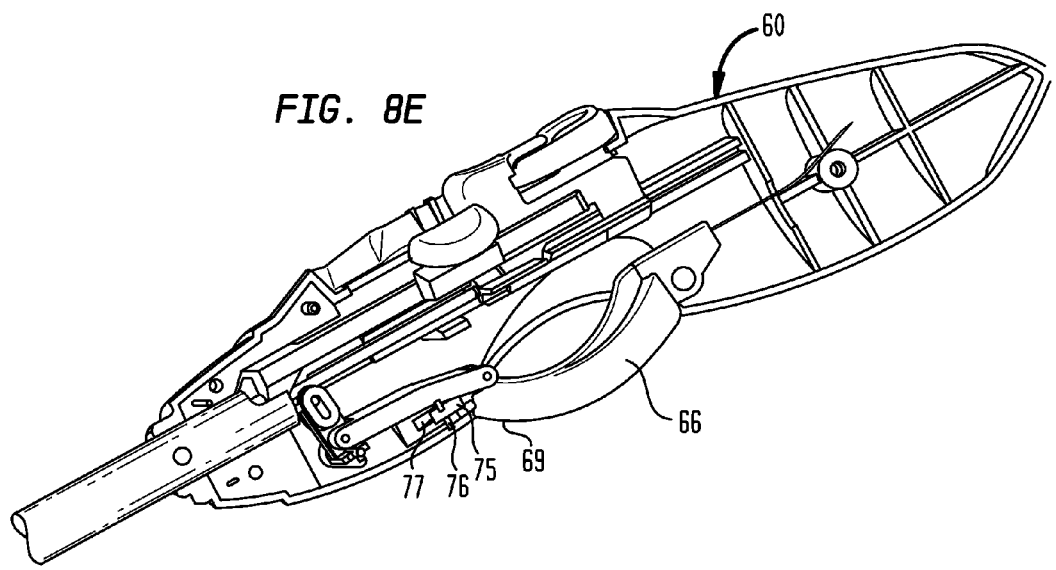

Referring again to FIGS. 2B and 2C, a safety catch 75 may be connected to the handle 60 by a pivot pin 76, such that the safety catch may rotate between a locked position (FIGS. 8D and 8E) that prevents actuation of the third button 66 and an unlocked position (FIG. 10D) that frees the third button for actuation.

Figure 10B:
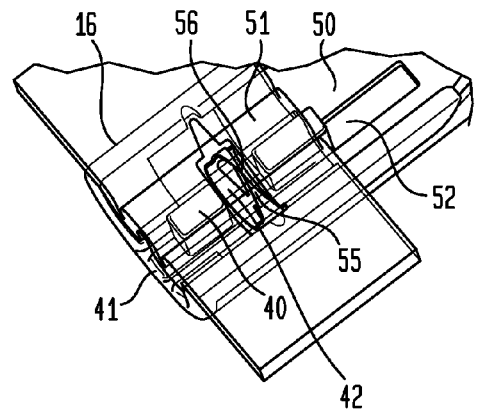
FIG. 10B is a view similar to FIG. 8A, but shown with the clip in a partially-deployed position.

To use the device 10 for transcatheter gathering of heart valve leaflet tissue, a user may first actuate the third button 66 of the handle 60 to retract the fingers 51 of the retaining arm 50 proximally of the gap 42 between the anvil portions 40a and 40b (FIG. 10B). A clip 55 may then be loaded into the gap 42, and the third button 66 released. The spring 68 will then bias the third button 66 back to its initial position, whereupon the retaining arm 50 will slide distally until the fingers 51 thereof cover the clip 55 and hold it in place.

Next, referring to FIG. 2A, the distal portion 14 of the catheter assembly 12 may be inserted into a patient through the apex of the heart, for example, into the left ventricle, so that the distal portion extends between the posterior leaflet 2 and the anterior leaflet 3 of the mitral valve 1. As shown in FIG. 2A, the distal edge 17 of the outer tube 16 may be disposed approximately at the coaption line 5 of the mitral valve 1, with the open side of the outer tube 16 facing the posterior leaflet 2. In a particular embodiment, the distal edge 17 of the outer tube 16 may be guided to a position at the coaption line 5 using the assistance of three-dimensional echocardiography to visualize the outer tube or other components of the catheter assembly 12.

Then, referring to FIG. 3, the containment tube 20 may be deployed by sliding the first and second portions 62 and 63 of the first button 61 together distally from an initial position (shown in FIG. 2B) to a deployed position. The distal movement of the first button 61 moves the tip 21 of the containment tube 20 beyond the distal end 17 of the outer tube 16, such that the tip 21 extends above the coaption line 5.

Figure 4C:
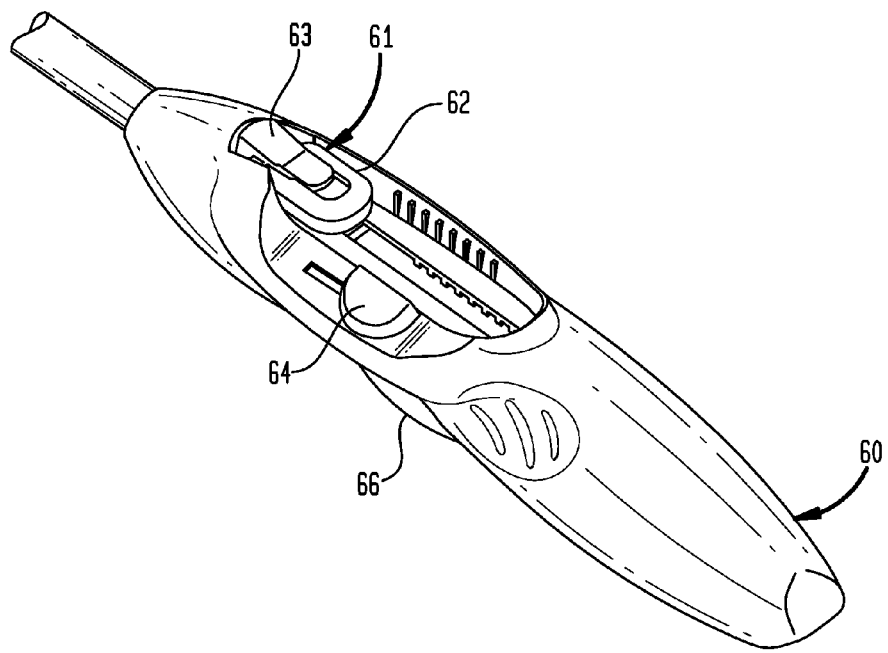
FIGS. 4C and 4D are a perspective view and a longitudinal cross-sectional view of the handle of FIG. 2B, shown with the buttons positioned to correspond to the positions of the components of the device shown in FIG. 4A.
Figure 4D:
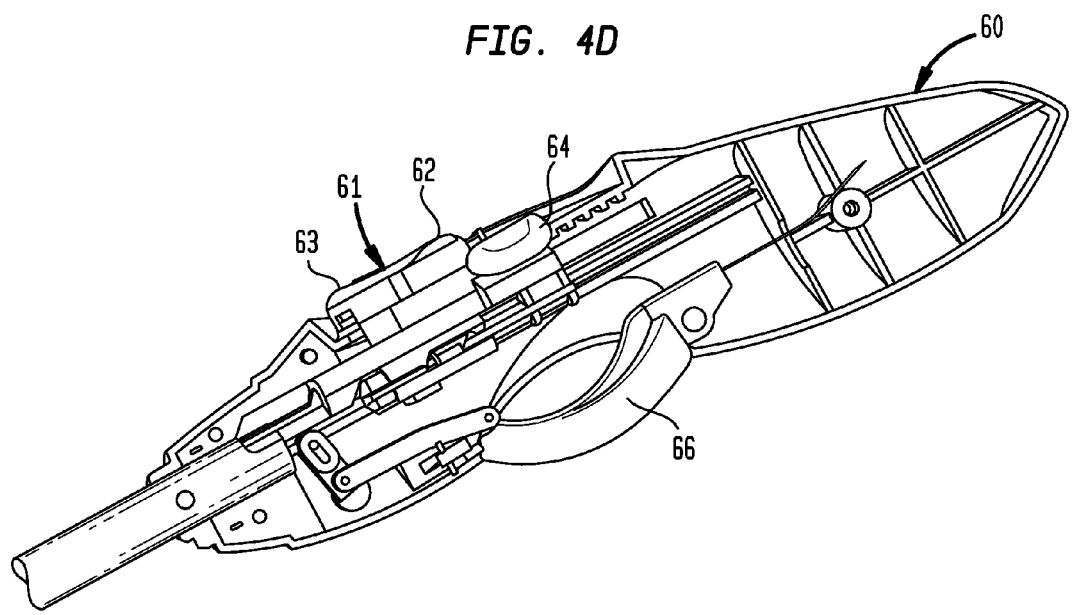

Referring to FIGS. 4A and 4B, the hook 24 may then be deployed to an extended position by sliding the second portion 63 of the first button 61 distally relative to the first portion 62 from an initial position (shown in FIG. 2B) to a deployed position (shown in FIGS. 4C and 4D). The distal movement of the second portion 63 relative to the first portion 62 moves the distal portion 23 of the grasping wire 22 out of the containment tube 20. No longer being constrained by the containment tube 20, the distal portion 23 of the grasping wire 22 may assume the curved shape of the hook 24.

Figure 5A:
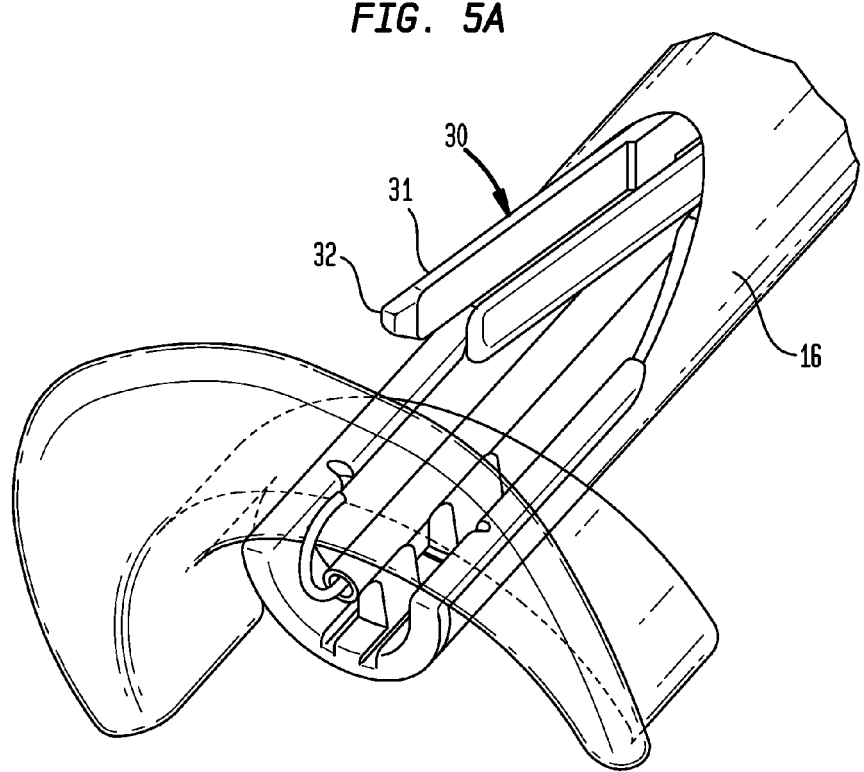
FIGS. 5A and 5B are a perspective view and a longitudinal cross-sectional view of the distal portion of the device of FIG. 2A, shown with the fork partially deployed.
Figure 5B:
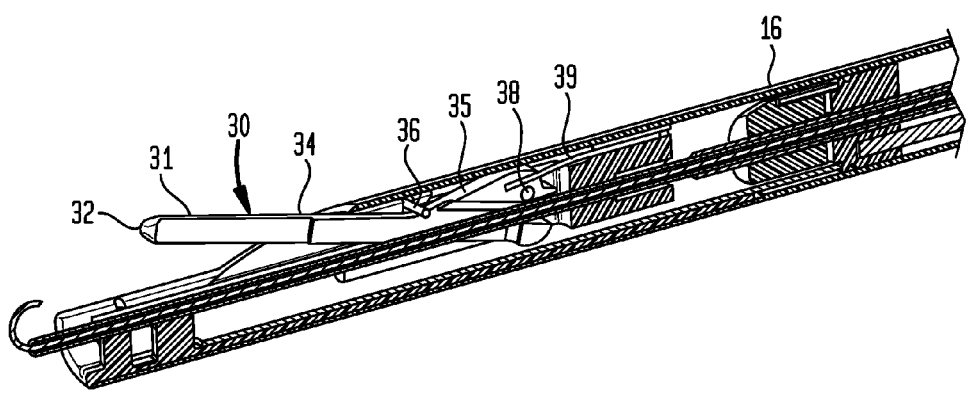

The fork 30 may then be partially deployed by sliding the second button 64 distally from an initial position (shown in FIG. 4C) to an intermediate position (not shown). As shown in FIGS. 5A and 5B, the distal movement of the second button 64 moves the fork 30 distally relative to the outer tube 16. As the fork 30 moves distally, the spring 39 will continue to exert a rotational force to the fork (in the clockwise direction of FIG. 5B), forcing the first cam surface 34 of each tine 31 against the pin 36. The distal movement of the cam surface 34 against the pin 36 will allow the ends 32 of the tines 31 to move gradually away from the closed side 41 of the outer tube 16 and away from the anvil 40.

Figure 6A:
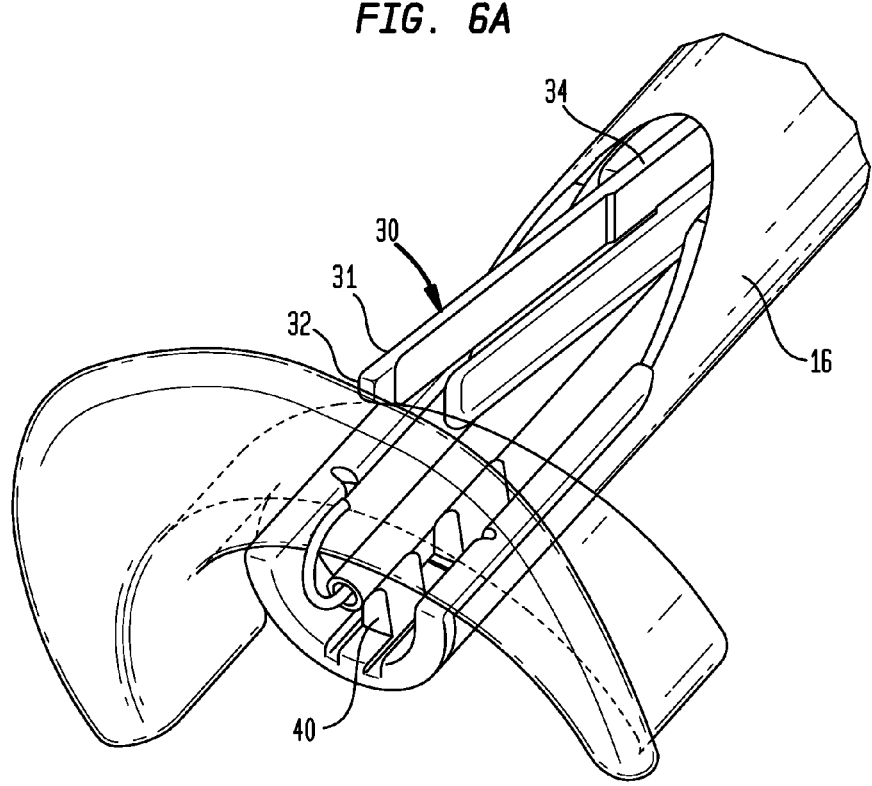
FIGS. 6A and 6B are a perspective view and a longitudinal cross-sectional view of the distal portion of the device of FIG. 2A, shown with the fork in the support position.
Figure 6B:
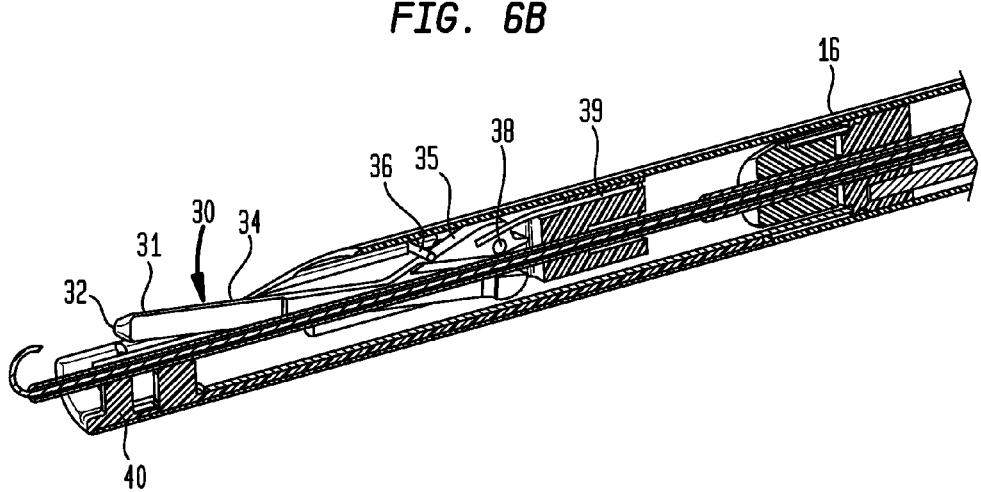
Figure 6C:
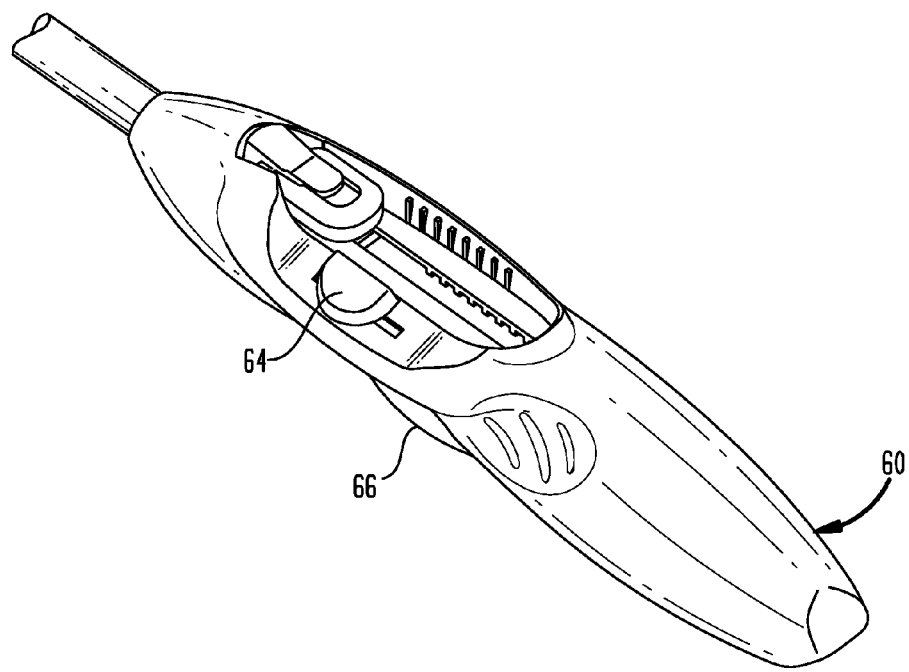
FIGS. 6C and 6D are a perspective view and a longitudinal cross-sectional view of the handle of FIG. 2B, shown with the buttons positioned to correspond to the positions of the components of the device shown in FIG. 6A.
Figure 6D:
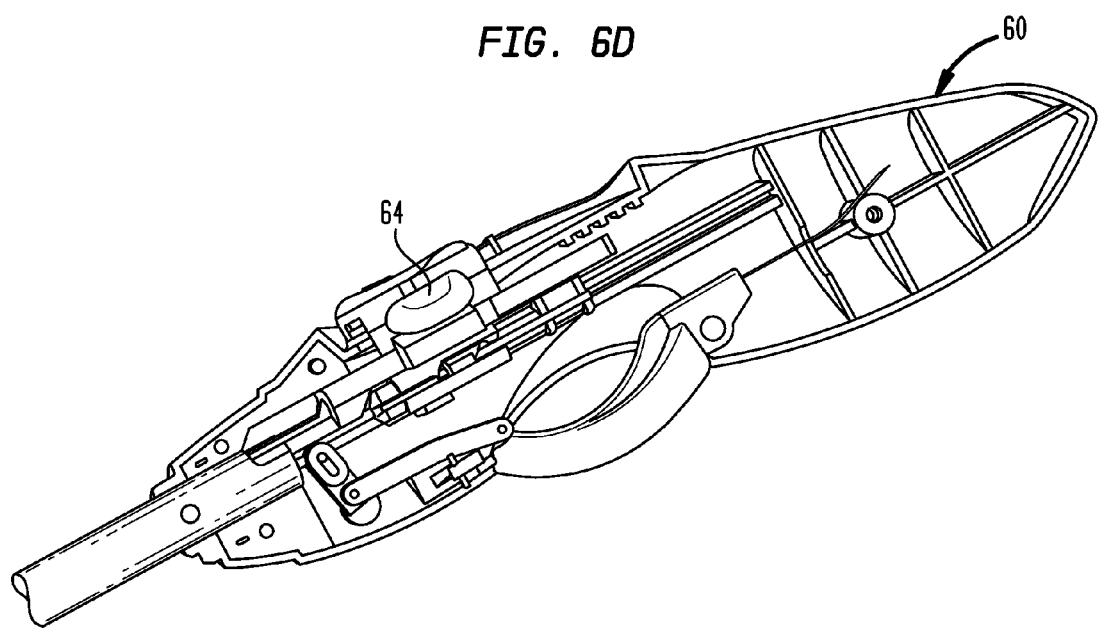

The fork 30 may continue to be deployed toward an open position by further movement of the second button 64 in the distal direction. As the fork 30 advances, the ends 32 of the tines 31 will continue to move laterally away from the closed side 41 of the outer tube 16 until the pin 36 reaches the intersection of the cam surfaces 34 and 35. Because the cam surface 35 is at a different angle than the cam surface 34, the interaction of the pin 36 and the cam surface 35 will exert a rotational force in the opposite direction as the fork continues to advance. That is, as the fork 30 moves further distally, the pin 36 will exert a downward force tending to rotate the fork in the opposite direction (i.e., counterclockwise in FIG. 6B). As this latter force is greater than the rotation force exerted by spring 39, further distal movement of the fork 30 will cause the ends 32 of the tines 31 to move laterally towards the closed side 41 of the outer tube 16 and towards the anvil 40.

Figure 7A:
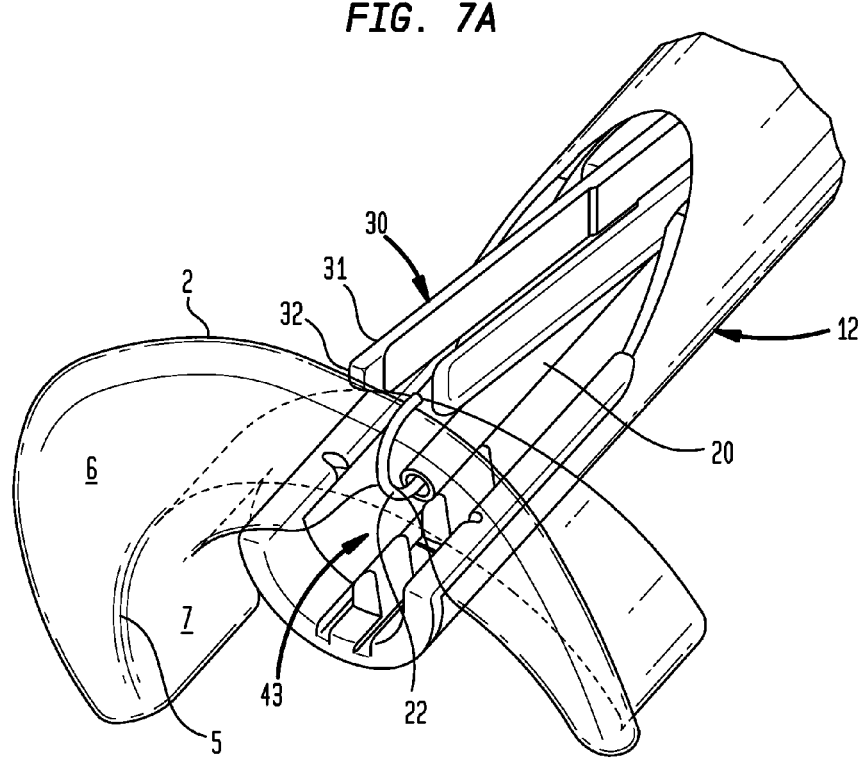
FIG. 7A is a perspective view of the distal portion of the device of FIG. 2A, shown with the hook in the partially-retracted position and the fork in the support position.
Figure 7B:
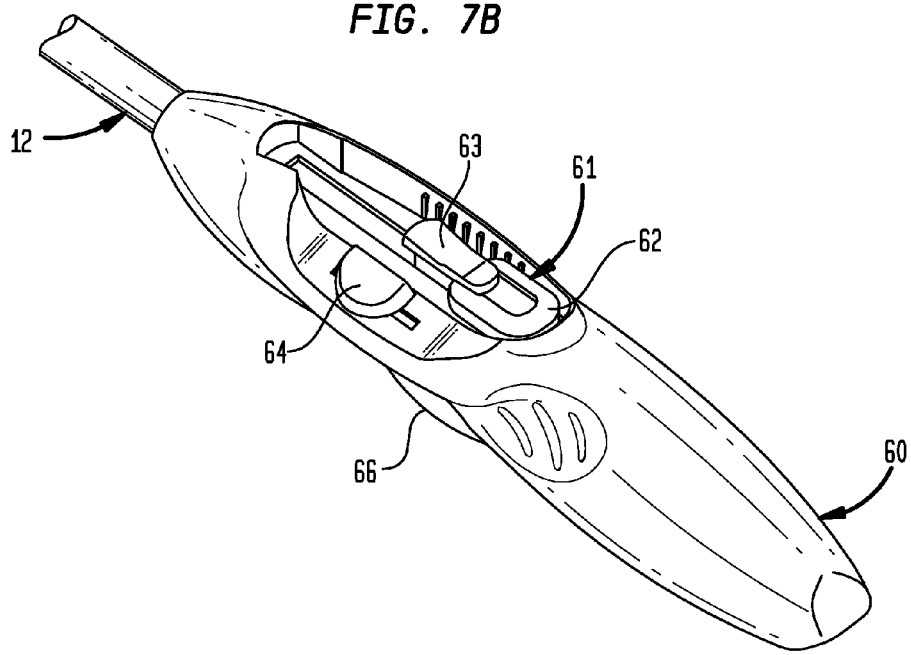
FIG. 7B is a perspective view of the handle of FIG. 2B, shown with the buttons positioned to correspond to the positions of the components of the device shown in FIG. 7A.

Referring to FIGS. 7A and 7B, the hook 24 may be partially retracted against the tissue of the posterior leaflet 2 by sliding the first and second portions 62 and 63 of the first button 61 together proximally (FIG. 7B). The proximal movement of the first button 61 partially retracts both the containment tube 20 and the grasping wire 22, such that the hook 24 engages against the upper surface 6 of the posterior leaflet 2 and pulls tissue of the leaflet into the space 43 between the containment tube and the tines 31 of the fork 30.

Figure 10C:
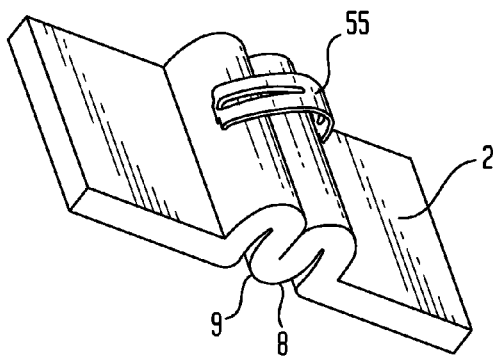
FIG. 10C is a diagrammatic view of the clip and the posterior mitral valve leaflet of FIG. 10B, shown with the clip in a partially-deployed position.
Figure 10D:
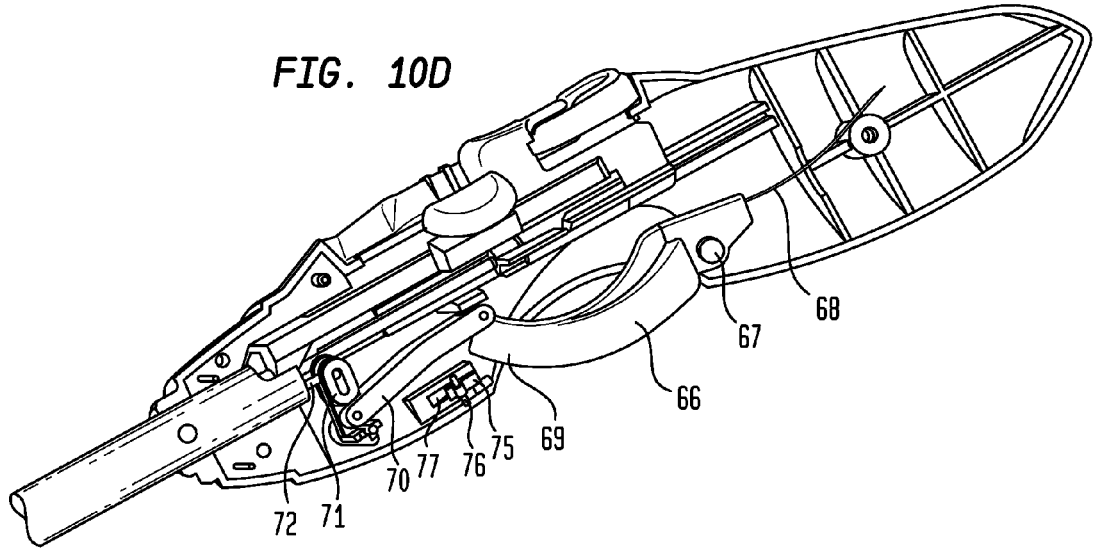
FIG. 10D is a longitudinal cross-sectional view of the handle of FIG. 2B, shown with the buttons positioned to correspond to the positions of the components of the device shown in FIG. 10A.

The tissue captured in the space 43 may be clamped between the anvil 40 and the tines 31 of the fork 30 by further sliding of the second button 64 distally to the fully deployed position. The further distal movement of the second button 64 moves the fork 30 further distally relative to the outer tube 16. As the fork 30 advances further toward a closed position adjacent the anvil 40, the interaction of the second cam surface 35 with the pin 36 will force the tines 31 of the fork toward the anvil and the closed side 41 of the outer tube 16, squeezing the captured tissue 9 therebetween. Continued movement of the fork 30 toward the anvil 40 will force the captured tissue 9 into the space 33 between the tines 31, and into the spaces between the tines and the closed side 41 of the outer portion 16. A W-shaped pleat 8 (FIG. 10C) will thus be formed in the captured tissue 9, with the raised center portion of the W overlying the anvil 40, and the two lower portions of the W lying between the tines 31 and the closed side 41 of the outer tube 16. By forming a W-shaped pleat 8, most or all of the portion of the posterior leaflet 2 that is billowed, loose, or floppy may be gathered and tightened.

With the tissue captured, the retaining arm 50 may be retracted by releasing the catch 75 and actuating the third button 66 by depressing it toward the handle 60. The retaining arm 50 may be retracted until the fingers 51 thereof are proximal of the gap 42 in the anvil 40 (FIG. 10B). At this juncture, the fingers 51 will no longer overlie the clip 55, such that the two prongs 56 of the clip will be free to spring away from the closed surface 41 of the outer tube 16 and become embedded in the captured tissue 9 of the posterior leaflet 2, thereby securing the tissue in the pleated form.

At this point, the clip 55 may be only partially engaged into the posterior leaflet 2 because the tines 31 of the fork 30 are positioned within the folds of the pleat 8. In a particular example, the clip 55 may be engaged in the lower portion 7 of the posterior leaflet 2 close to the coaption line 5. Optionally, a suture, such as the suture 258 described below with respect to FIGS. 16A and 16B, may extend from the clip 55 to the catheter assembly 12 so that the clip may be retrieved using the device 10, for example, if the clip has been installed at a sub-optimal location in the posterior leaflet 2 or does not become adequately embedded in the tissue. A user may desire to disengage the clip from the tissue and deploy another one.

After the clip 55 has been adequately secured in the tissue of the posterior leaflet 2, the device 10 may be withdrawn from the patient. To withdraw the device 10, the hook 24 may first be withdrawn from engagement with the posterior leaflet 2 by retracting the second portion 63 of the first button 61 relative to the first portion 62 thereof. This action causes the hook 24 to straighten as the grasping wire 22 retracts into the containment tube 20.

Next, the fork 30 may be withdrawn from within the clip 55. To withdraw the fork 30, the second button 64 may be moved proximally, thereby moving the fork proximally relative to the outer tube 16. While the fork 30 moves proximally, the spring 39 will exert a rotational force to the fork (in the clockwise direction of FIG. 8B), forcing the second cam surface 35 against the pin 36. The proximal movement of the cam surface 35 against the pin 36 will allow the ends 32 of the tines 31 to move gradually away from the closed side 41 of the outer tube 16 and away from the anvil 40. As the fork 30 continues to move proximally, the ends 32 of the tines 31 will continue to move laterally away from the closed side 41 of the outer tube 16 until the pin 36 reaches the intersection of the cam surfaces 34 and 35. Because the cam surface 35 is at a different angle than the cam surfaces 34, the interaction of the pin 36 and the cam surfaces 34 will exert a rotational force in the opposite direction as the fork 30 continues to move proximally. That is, as the fork 30 moves further proximally, the pin 36 will exert a downward force tending to rotate the fork in the opposite direction (i.e., counterclockwise in FIG. 5B). As this latter force is greater than the rotation force exerted by spring 39, further proximal movement of the fork 30 will cause the ends 32 of the tines 31 to move laterally towards the closed side 41 of the outer tube 16, thereby enabling the fork 30 to retract into the outer tube.

Once the fork 30 has disengaged from within the clip 55, the two prongs 56 of the clip may become more tightly embedded in the posterior leaflet 2, such that the two prongs may cross one another, thereby allowing the clip to extend along an arc that is greater than 360 degrees. Finally, the catheter assembly 12 may be withdrawn from the patient through the apex of the heart. The procedure described above may be repeated to apply one or more additional clips 55 onto the same posterior leaflet 2.

An alternate embodiment of a device 210 for transcatheter gathering of heart valve leaflet tissue is shown in FIGS. 11A-11C. The device 210 is similar to the device 10 shown above, but rather than having a clamping member press tissue against an anvil to obtain a desired tissue configuration, a hook pulls tissue into a longitudinal slot formed in the outer tube 216 that configures the captured tissue into a pleat.

The outer tube 216 has opposed U-shaped longitudinal slots or channels 215 for folding and capturing tissue into a pleated configuration. The U-shaped channels 215 each extend proximally from the distal edge 217 of the outer tube 216 in a longitudinal direction substantially parallel to the longitudinal axis of the outer tube. Each channel 215 has a closed end 219 located in the distal portion 211 of the outer tube and an open end 213 adjacent the distal edge 217 of the outer tube 216. The distal edge 217 of the outer tube 216 may have angled portions 227 each oriented at an oblique angle relative to the longitudinal axis Y of the outer tube. As can be seen most easily in FIG. 12B, the angled portions 227 may form a substantially V-shaped opening or notch 229 leading to the U-shaped slot 215. In alternative embodiments such as the embodiment shown in FIG. 16, the device may be provided with a single U-shaped slot 215 disposed remote from a containment tube 220.

Figure 13A:
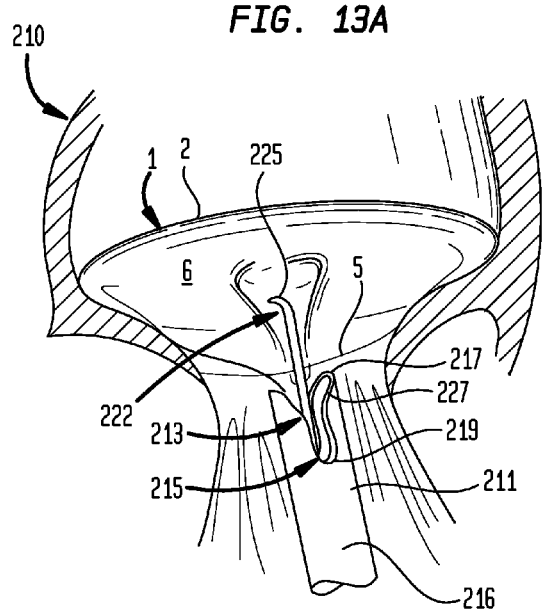
FIG. 13A is a diagrammatic view of the distal portion of the device of FIG. 11A, shown engaged with the posterior leaflet of the mitral valve and with the hook deployed.

Similar to the device 10 described above, the device 210 further includes a capture tool in the form of a grasping wire 222 that is longitudinally slidable within the containment tube 220 between a retracted position substantially entirely within the lumen of the containment tube (FIG. 11B), and a deployed position in which a distal portion of the grasping wire protrudes from the distal tip of the containment tube (FIG. 13A). The grasping wire 222 may have a linear configuration when fully retracted within the containment tube 220 and the distal portion thereof may assume the shape of a hook 225 when deployed from the containment tube. In that regard, the grasping wire 222 may be formed from a memory metal or a strong, resilient metal or polymer that will cause the hook 225 to form automatically when deployed.

The device 210 may include one or more tissue securing components in the form of clips 255 disposed within the outer tube 216. It is preferred that the containment tube 220 be located adjacent one of the slots 215, to maximize the portion of the outer tube 216 that can be used to store the clip 255. The clip 255 (FIG. 11D) may be wholly or partly made of a shape-memory material or a resilient material and may be biased to curl into a substantially round closed configuration (FIG. 11C) when the clip is not being held open, as described below. Prongs 257 and 259 at opposite ends of a central portion 258 of the clip 255 may be adapted to become embedded in the leaflet tissue when the clip is deployed. The clip 255 may define recesses 256 adjacent the prongs 257 and 259 that extend inward toward the central portion 258 of the clip. Although drawings illustrate a clip 255, the device 210 may include any other fastener suitable for fastening tissue.

The device 210 may also include a support shelf 260 that may be longitudinally slidable along the longitudinal axis Y of the outer tube 216 between a retracted position in which a distal end 262 of the support shelf is disposed within the outer tube (FIG. 11A) and an extended position in which the distal end of the support shelf is disposed beyond the distal end 217 of the outer tube (FIG. 14A). The distal end 262 of the support shelf 260 may be adapted to support the central portion 258 of the clip 255. In the embodiment shown in the figures, the distal end 262 of the support shelf 260 is planar, but in other embodiments (not shown), the distal end of the support shelf may be curved to approximately match the curvature of the central portion 258 of the clip 255 in the partially-open configuration shown in FIGS. 12A and 12B or the substantially round closed configuration shown in FIG. 11C.

A plurality of expansion hooks 270 may be provided that are adapted to retain the clip 255 in the partially-open configuration shown in FIGS. 12A and 12B, such that the prongs 257 and 259 of the clip are separated by a gap 273. As can be seen in FIG. 11B, there may be four expansion hooks 270, each adapted to engage a corresponding one of the recesses 256 of the clip 255. The expansion hooks 270 may each have an actuation portion 272 that extends from the hooked portion to a proximal end of the device for actuation by a user. The expansion hooks 270 may each be slidable along the longitudinal axis Y of the outer tube 216. The expansion hooks 270 may be made of a metal such as nitinol, for example.

The device 210 can be used for transcatheter gathering of heart valve leaflet tissue in a manner similar to the device 10 described above, and it may be controlled by a handle similar to the handle 60 of FIG. 2B.

To load a clip 255 into the outer tube 216, the support shelf 260 may be moved to a partially retracted position or the fully retracted position shown in FIG. 11A, and the clip may be placed onto the distal end 262 of the support shelf 260. The expansion hooks 270 may each be engaged in a corresponding one of the recesses 256 of the clip 255, and the actuation portion 272 of the expansion hooks may be pulled proximally to move the clip 255 from the substantially round closed configuration shown in FIG. 11A to the partially-open configuration shown in FIGS. 12A and 12B, thereby separating the prongs 257, 259 from one another with a gap 273 therebetween. The hooks 270 may remain tensioned until it is desired to deploy the clip 255 into captured leaflet tissue. It is preferred that the clip be opened wide enough that the gap 273 between the opposed prongs 257, 259 is equal to or greater than a width W of the slots 215, so that the captured leaflet tissue will not initially contact the prongs while the tissue is being pulled into the outer tube 216.

Next, the distal portion 211 of the outer tube 216 may be inserted into a patient through the apex of the heart, for example, into the left ventricle, so that the distal portion extends between the posterior leaflet 2 and the anterior leaflet 3 of the mitral valve 1. As shown in FIG. 13A, the distal edge 217 of the outer tube 216 may be disposed approximately at the coaption line 5 of the mitral valve 1, with the slot 215 that is remote from the containment tube 220 facing the posterior leaflet 2 (alternatively, if the anterior leaflet 3 is being repaired, the slot that is remote from the containment tube may face the anterior leaflet).

Then, still referring to FIG. 13A, the hook 225 may be deployed to an extended position above the coaption line 5 by sliding the distal portion of the grasping wire 222 distally out of the containment tube 220 until the hook lies beyond the distal edge 217 of the outer tube 216. No longer being constrained by the containment tube 220, the distal portion of the grasping wire 222 may assume the curved shape of the hook 225.

Figure 13B:
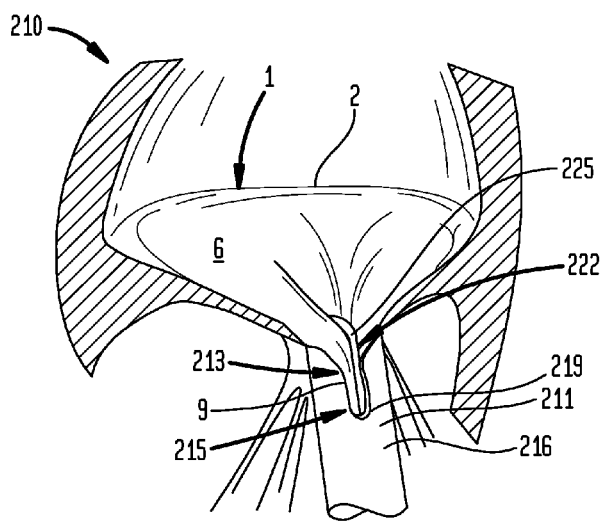
FIG. 13B is a diagrammatic view of the distal portion of the device of FIG. 11A, shown with the hook in a partially-retracted position.

Referring to FIG. 13B, the hook 225 may be partially retracted against the tissue of the posterior leaflet 2 by moving either the grasping wire 222 or both the containment tube 220 and the grasping wire proximally, such that the hook 225 engages against the upper surface 6 of the posterior leaflet 2 and pulls tissue of the leaflet into the outer tube 216. The containment tube 220 and the grasping wire 222 may be moved proximally using the handle 60, as described above with reference to the device 10.

Figure 13C:
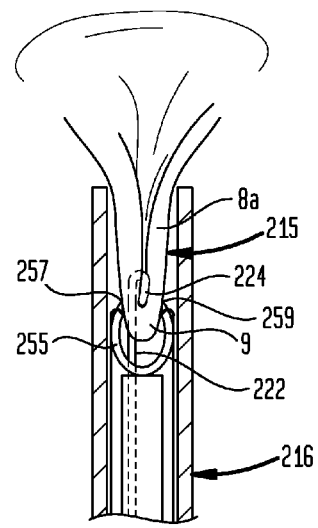
FIG. 13C is a diagrammatic view of the distal portion of the device of FIG. 11A, shown with the hook in a fully-retracted position.

Referring to FIG. 13C, the hook 225 may be moved further proximally until the captured tissue 9 is pulled into one or both of the slots 215. The V-shaped opening 229 of each slot 215 may facilitate insertion of the tissue into the slots. As the captured tissue 9 is forced into the slots 215, the captured tissue will be formed or folded into substantially a U-shaped pleat 8a that at least partially conforms to the shape of the slots. By forming a U-shaped pleat 8a, most or all of the portion of the posterior leaflet that is billowed, loose, or floppy may be gathered and tightened. It is preferred that the captured tissue 9 be pulled distally until at least a portion of the U-shaped pleat 8a extends into the gap 273 between the opposed prongs 257, 259 of the clip 255.

With the tissue captured, the clip 255 may be deployed into the captured tissue 9 by reducing the tension on the expansion hooks 270. Once the tension is reduced, the bias of the clip 255 will force the prongs 257, 259 to become embedded into the captured tissue 9, thereby securing the tissue in the pleated form, as shown in FIGS. 14A and 14B.

After the clip 255 has been adequately secured in the tissue of the posterior leaflet 2, the device 210 may be withdrawn from the patient. To withdraw the device 210, the hook 225 may first be withdrawn from engagement with the posterior leaflet 2 by retracting the hook distally. This action causes the hook 225 to straighten as the grasping wire 222 retracts into the containment tube 220.

Next, the clip 255 may be released from the device 210 by sliding the support shelf 260 and the hooks 270 distally until the clip is moved out of the outer tube 216. Then, the hooks 270 may be released from the corresponding recesses 256 of the clip by sliding the actuation portion 272 of each clip distally until the hooks become disengaged from the recesses. After the clip 255 has been fully released from the device 210, the device may be withdrawn from the patient, as discussed above with respect to the device 10.

In an alternative embodiment, a device 210' shown in FIG. 15A may be the same as the device 210 described above, except the hooks 270 may be replaced by sutures 290, and cutting tubes 292 may be provided to detach the sutures from the clip 255'. As shown in FIG. 15B, the clip 255' may be provided with apertures 253 adjacent the prongs 257 and 259, and the sutures 290 may be fastened onto the clip by being knotted through the apertures.

The suture cutting tubes 292 may be telescopically mounted within the outer tube 216 and around the sutures 290 for sliding movement between a retracted position with the distal end 293 of each cutting tube generally adjacent the distal end 262 of the support shelf 260 (as shown in FIG. 15A), and a deployed position in which a distal portion of the suture cutting tube protrudes distally beyond the distal end of the support shelf. The suture cutting tubes 292 may each have a sharp distal end 293 that is configured to cut through a portion of corresponding suture 290. The sutures 290 may be resorbable, so that the distal most portion of the sutures 290 that remain knotted to the clip 255' can be resorbed into the patient.

Figure 16:
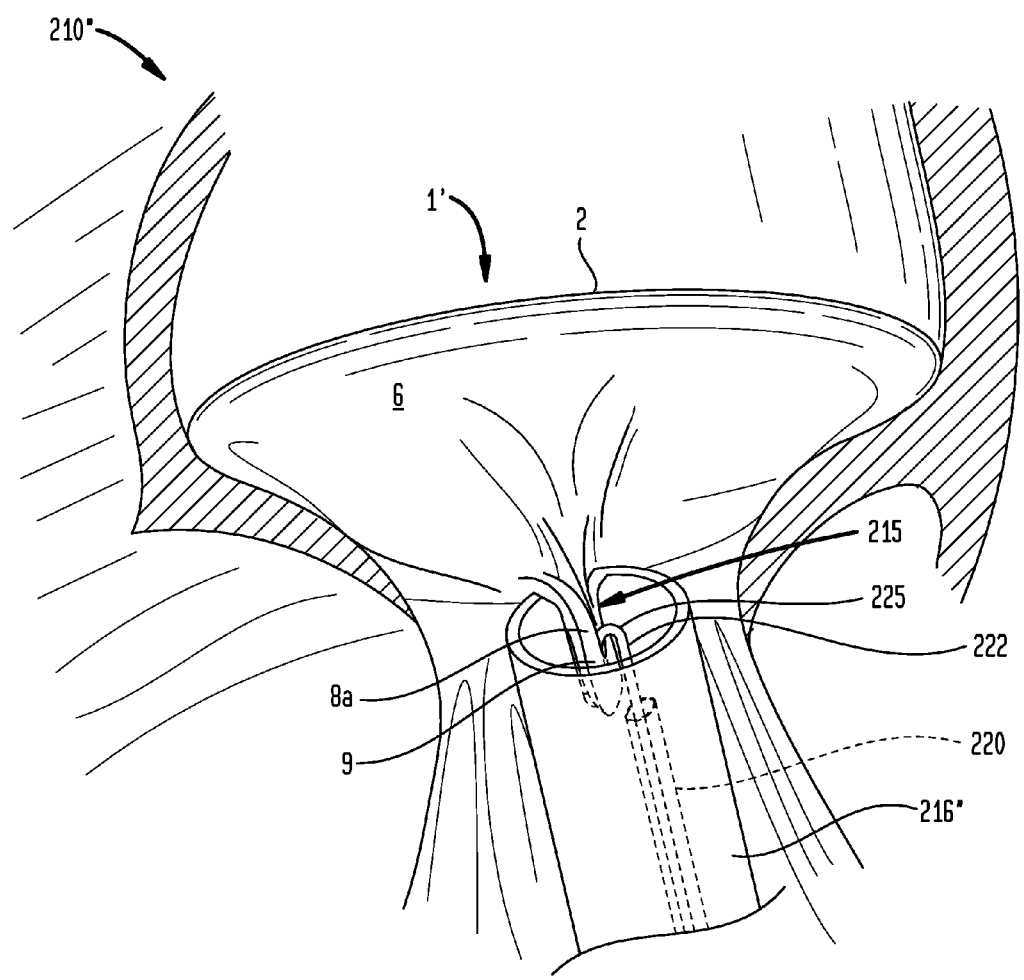
FIG. 16 is a diagrammatic view of the distal portion of a variation of the device of FIG. 11A with an outer tube having a single slot.

In another alternative embodiment, a device 210" shown in FIG. 16 may be the same as the device 210 described above, except that the device 210" has a single U-shaped slot 215 disposed remote from the containment tube 220. The device 210" can be used for transcatheter gathering of heart valve leaflet tissue in a manner similar to the device 210 described above, and it may be controlled by a handle similar to the handle 60 of FIG. 2B. The device 210" can function the same way as the device 210 described above, except that when the hook 225 pulls tissue of the leaflet into the outer tube 216", the captured tissue 9 is pulled into the single slot 215. As the captured tissue 9 is forced into the single slot 215, the captured tissue will be formed or folded into substantially a U-shaped pleat 8a that at least partially conforms to the shape of the slot.

In the devices shown in the figures, particular structures are shown that are adapted to gather, secure, and repair heart valve leaflet tissue. The invention also contemplates the use of any alternative structures for such purposes, including structures having different lengths, shapes, and configurations. For example, although the capture tool is shown in the form of a grasping wire 22 or 122, the capture tool may take other forms, including for example, a pincer-like structure such as a clamp. Although the clamping member is shown in the form of a fork 30, the clamping member may have other configurations, such as an arm having a curved surface such that outer edges of the arm can serve as tines, a lattice structure, or any other structure capable of retaining leaflet tissue against the anvil 40 and the closed surface 41 of the outer shaft 16. The tissue support is shown as an anvil 40, but may take other forms, such as a corrugated surface, a set of pins extending from the closed surface 41 of the outer shaft 16, or any other shape that can guide leaflet tissue into a desired shape onto which a clip 55 can be attached.

In another example, although the catheter assembly is described as being controllable by the movement of a particular configuration of buttons 61, 64, and 66 of a handle 60, any mechanisms that are adapted to control the movement and deployment of the containment tube, grasping wire, fork, and clip may be used. Furthermore, although the grasping wires 22 and 122 are shown as having a hook 24 and a dog-leg arm 125, respectively, the distal portion of the grasping wire may have any shape or configuration that may be adapted to grasp a target portion of valve leaflet tissue and help to capture such tissue inside or adjacent the outer tube such that a clip may be applied to the captured tissue.

Moreover, although the fork 30 is described as having two tines 31 that cooperate with the anvil 40 to capture leaflet tissue and form same into a W-shaped pleat, the invention contemplates forks having any number of tines cooperating with any number of anvils to form any number of pleats in the captured tissue. For example, a fork having a single tine may cooperate with two anvils that are laterally spaced apart from one another to form leaflet tissue into a pleat. It will be appreciated that the more pleats that are formed, the more the tissue of the valve leaflet can be tightened. In a particular embodiment, the tissue capture mechanism may include an outer tube 16 without an anvil portion extending from the inner surface 41 of the outer tube, wherein the tines 31 of the fork 30 are adapted to capture leaflet tissue in a single contiguous space defined within the outer tube 16, such that a portion of the inner surface of the outer tube may serve as an anvil portion. In such an embodiment without an anvil portion extending from the inner surface 41 of the outer tube 16, the hook 24 and the containment tube 20 may serve as an anvil portion to cooperate with the fork 30 to form leaflet tissue into a W-shaped pleat.

Although the fork 30 is described as including cam surfaces 34 and 35 for controlling lateral movement of the tines 31 as the fork is moved distally and proximally relative to the outer tube 16, other mechanisms may be used for controlling such lateral movement of the tines. For example, cam surfaces located at any location along the fork may slide against any portion of the outer tube 16 or any surface projecting therefrom to control lateral movement of the tines. Alternatively, a mechanism controlled by a dedicated button of the handle may be used to actuate lateral movement of the tines relative to the outer tube 16.

Although the device 10 is shown as being adapted to apply a single clip 55 onto a posterior leaflet 2, the invention contemplates devices that are adapted to apply a plurality of clips to the leaflet tissue during a single insertion of the device into a patient. For example, the gap 42 between the anvil portions 40*a* and 40*b* may be sufficiently large to accommodate a plurality of clips 55 in side-by-side relationship. In such an embodiment, while leaflet tissue is captured within the outer tube 16, the retaining arm 50 may be retracted to a first position to apply a first clip 55 to the tissue at a first target location, and the retaining arm may then be further retracted to a second position to apply a second clip 55 to the tissue at a second target location spaced from the first location.

Although the various delivery devices have been described herein in connection with tightening the posterior leaflet of a mitral valve, all of the delivery devices may be used on other heart valve leaflets, such as the anterior leaflet of the mitral valve, or on any other tissue of the body for which a reduction in the length of the tissue would be beneficial.

Although the invention herein has been described with reference to particular embodiments in which the catheter assembly is inserted into the patient via an introducer and through the apex of the heart (i.e., transapical insertion), it is to be understood that the invention contemplates embodiments in which the catheter assembly extends through a portion of the vasculature of the patient to reach the heart, for example, through a transfemoral or subclavian artery. In such embodiments, some of the device components may have to be oriented in a different direction to that described herein. For example, the invention contemplates embodiments in which the distal portion of the catheter assembly approaches the mitral valve from the upstream side as well as from the downstream side of the valve.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for transcatheter gathering of tissue of a heart valve leaflet, comprising:
an elongated tube extending in a longitudinal direction and having a circumferential wall and at least one slot extending through the wall and extending generally in the longitudinal direction from a distal end of the elongated tube, the at least one slot having an open end at the distal end of the elongated tube and a closed end remote therefrom;
a capture tool moveable in the elongated tube between a retracted position and an extended position, the capture tool being operable to gather tissue of the heart valve leaflet into the at least one slot, such that the gathered tissue has a pleated configuration;
a tissue securing component disposed within the elongated tube and adapted to be applied to the gathered tissue for holding the gathered tissue in the pleated configuration, the tissue securing component comprising a clip arrangeable in a partially-open condition within the elongated tube and biased to contract to a clamping condition when deployed from the elongated tube; and
retention elements adapted to hold the clip in the partially-open condition, the retention elements including hooks adapted to engage with recesses at opposed ends of the clip.

2. The device of claim 1, wherein a distal end of the capture tool has a hook shape.

3. The device of claim 2, wherein the capture tool includes a grasping wire slidably disposed in a containment tube, and a distal portion of the grasping wire is adapted to change from a linear shape to the hook shape when the distal portion of the grasping wire is extended out from the containment tube.

4. The device of claim 3, wherein the grasping wire is partially or entirely made from a shape-memory material.

5. The device of claim 1, further comprising an operating handle having an actuating member adapted to control movement of the capture tool between the retracted and extended positions.

6. The device of claim 1, wherein at least a portion of the at least one slot has a generally U-shaped configuration.

7. The device of claim 6, wherein the elongated tube has at least one pair of opposed angled portions, each pair of opposed angled portions extending between the distal end of the elongated tube and sidewalls of a corresponding one of the at least one slot, each pair of angled portions forming at least a portion of a substantially V-shaped opening leading to the at least one slot.

8. The device of claim 1, wherein the at least one slot includes two slots located substantially opposite one another in a direction perpendicular to the longitudinal direction of the elongated tube.

9. The device of claim 1, wherein the clip is wholly or partly made of a shape-memory material.

10. The device of claim 1, further comprising a support shelf slidable within the elongated tube in the longitudinal direction between a retracted position in which a distal end of the support shelf is disposed within the elongated tube and an extended position in which the distal end of the support shelf is disposed beyond the distal end of the elongated tube, the support shelf being adapted to support the clip within the elongated tube.

11. The device of claim 10, wherein the clip in the partially-open condition has a generally cylindrical shape and defines a longitudinal axis around which the clip extends, the retention elements adapted to hold the clip in the partially-open condition with the longitudinal axis of the clip oriented substantially perpendicular to the longitudinal direction.

12. A device for transcatheter gathering of tissue of a heart valve leaflet, comprising:
an elongated tube extending in a longitudinal direction;
a releasable clip disposed within the elongated tube and adapted to be applied to gathered tissue for holding the gathered tissue in a gathered configuration, the clip being arrangeable in a partially-open condition within the elongated tube and biased to contract to a clamping condition when deployed from the elongated tube, the clip in the partially-open condition having a generally cylindrical shape and defining a longitudinal axis around which the clip extends;
a support shelf slidable within the elongated tube in the longitudinal direction between a retracted position in which a distal end of the support shelf is disposed within the elongated tube and an extended position in which the distal end of the support shelf is disposed beyond a distal end of the elongated tube, the support shelf being adapted to support the clip within the elongated tube; and a plurality of retention elements slidable within the elongated tube in the longitudinal direction, the retention elements being adapted to hold the clip in the partially-open condition with the longitudinal axis of the clip oriented substantially perpendicular to the longitudinal direction.

13. The device of claim 12, wherein the retention elements include sutures adapted to engage with apertures at opposed ends of the clip.

14. The device of claim 13, further comprising cutting tubes disposed around the sutures, the cutting tubes adapted to slide in the longitudinal direction relative to the elongated tube, the cutting tubes each having a sharp distal end adapted to cut through a portion of a corresponding one of the sutures.

15. The device of claim 12, further comprising a capture tool moveable in the elongated tube between a retracted position and an extended position, the capture tool being operable to draw the tissue of the heart valve leaflet into the elongated tube.

16. The device of claim 12, wherein the elongated tube has at least one slot extending generally in the longitudinal direction from a distal end of the elongated tube, the at least one slot having an open end at the distal end of the elongated tube and a closed end remote therefrom, the at least one slot adapted to form the gathered tissue into a pleated configuration.

17. The device of claim 12, wherein the retention elements are slidable between a retracted position in which a distal end of each retention element is disposed within the elongated tube and an extended position in which the distal end of each retention element is disposed beyond the distal end of the elongated tube.

\* \* \* \* \*